United States Patent
Silver

(10) Patent No.: US 11,819,296 B1
(45) Date of Patent: Nov. 21, 2023

(54) ADVANCED SYSTEM AND METHOD FOR A DEEP TISSUE MASSAGER

(71) Applicant: Alan H. Silver, Coral Springs, FL (US)

(72) Inventor: Alan H. Silver, Coral Springs, FL (US)

(73) Assignee: Alan Silver, Coral Springs, FL (US)

(*) Notice: Subject to any disclaimer, the term of this patent is extended or adjusted under 35 U.S.C. 154(b) by 1066 days.

(21) Appl. No.: 16/526,271

(22) Filed: Jul. 30, 2019

Related U.S. Application Data

(63) Continuation-in-part of application No. 16/041,202, filed on Jul. 20, 2018, now Pat. No. 11,109,918, which is a continuation of application No. 14/215,377, filed on Mar. 17, 2014, now Pat. No. 10,034,813.

(60) Provisional application No. 61/801,133, filed on Mar. 15, 2013.

(51) Int. Cl.
*A61B 34/30* (2016.01)
*A61H 7/00* (2006.01)

(52) U.S. Cl.
CPC ............ *A61B 34/30* (2016.02); *A61H 7/001* (2013.01); *A61H 7/007* (2013.01); *A61H 2201/0153* (2013.01); *A61H 2201/0176* (2013.01); *A61H 2201/1215* (2013.01); *A61H 2201/1481* (2013.01); *A61H 2201/1671* (2013.01); *A61H 2201/5061* (2013.01); *A61H 2201/5082* (2013.01)

(58) Field of Classification Search
CPC ...... A61H 7/00–002; A61H 7/004–005; A61H 23/00–02; A61H 23/0254–0263; A61H 2023/0281; A61H 39/007; A61H 2201/12–1223; A61H 2201/1671; A61B 34/30–77
See application file for complete search history.

(56) References Cited

U.S. PATENT DOCUMENTS

| | | | | |
|---|---|---|---|---|
| 4,175,548 | A * | 11/1979 | Henry | A61H 7/001 601/1 |
| 2004/0077978 | A1* | 4/2004 | Nelson | A61H 23/0263 601/70 |
| 2005/0166413 | A1* | 8/2005 | Crampton | G01B 5/008 33/503 |
| 2008/0300529 | A1* | 12/2008 | Reinstein | A61F 7/007 604/20 |
| 2009/0204061 | A1* | 8/2009 | Pomposelli | A61H 7/005 601/89 |
| 2009/0222024 | A1* | 9/2009 | Naldoni | A61B 17/54 606/131 |
| 2012/0071794 | A1* | 3/2012 | Karni | A61B 34/30 606/9 |
| 2018/0028772 | A1* | 2/2018 | Davis | A61M 16/06 |

* cited by examiner

*Primary Examiner* — Rachel T Sippel
(74) *Attorney, Agent, or Firm* — Fleit Intellectual Property Law; Jose Gutman

(57) ABSTRACT

A system, device, and method for therapeutic deep tissue massage are disclosed. The therapeutic deep tissue massage device includes an apparatus for use in therapeutic massage applications in which forces are provided to an outer surface of a body of a user, whether human or animal, and subcutaneously within the user's tissues. Sensors in the apparatus monitor various conditions of the environment and of the user. The data can be used to adjust the operation of the apparatus.

14 Claims, 17 Drawing Sheets

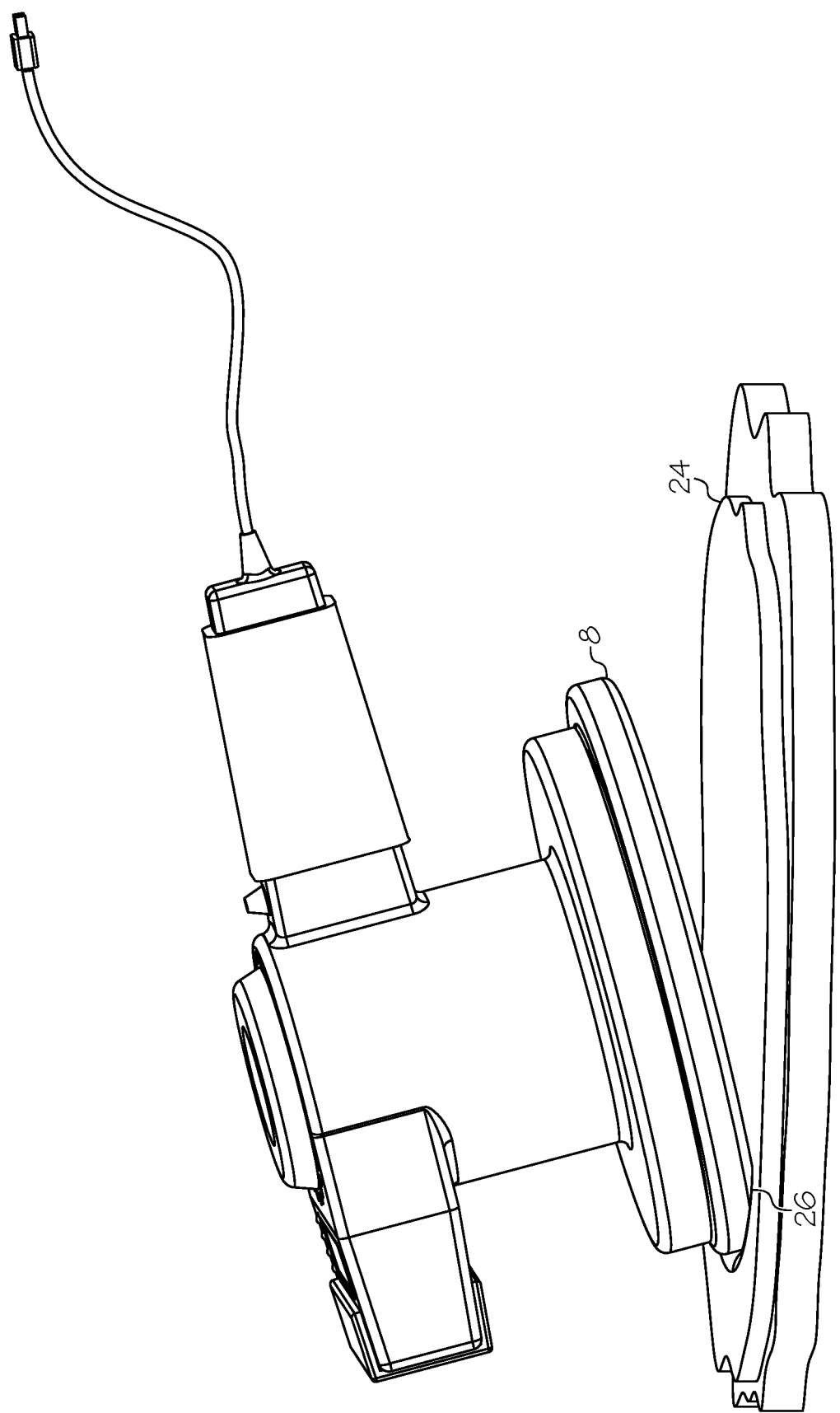

ADVANCED SYSTEM AND METHOD FOR A DEEP TISSUE MASSAGER

CROSS-REFERENCE TO RELATED APPLICATIONS

This application is a Continuation-in-Part of, and claims priority to, co-pending U.S. patent application Ser. No. 16/041,202, filed on Jul. 20, 2018, which is a Continuation of, and claims priority to, U.S. patent application Ser. No. 14/215,377, filed on Mar. 17, 2014, now U.S. Pat. No. 10,034,813, which was based upon and claimed priority to U.S. Provisional Patent Application Ser. No. 61/801,133, filed on Mar. 15, 2013, the collective disclosure thereof being hereby incorporated by reference in its entirety.

BACKGROUND

The present disclosure generally relates to deep tissue massagers, and more particularly relates to an apparatus and method for use in therapeutic massage applications in which forces are provided to an outer surface of the human body and subcutaneously within human tissues.

Traditional massage therapy has not changed significantly since its inception in 2330 BC. Frequently the daily demands placed on many humans today produces pain in the neck, shoulders, lower backs, legs and more. These pains are a result of overworked muscles that never fully return to a relaxed state, but instead are overworked repeatedly until they are contracted so as to better protect the muscle tissues to from being strained or torn. These repeated patterns of overuse frequently lead to a constant state of contraction or chronic muscle spasm.

Traditional massage therapy only relieves these problems for short periods of time, and is ineffective on deep muscle spasms unless numerous massages are scheduled over a period of days, weeks or months. Human Skin is comprised of a.) the epidermis, b.) the dermis, and c.) the hypodermis. More recent massage techniques employ the means to promote circulation within the blood and lymphatic vessels present in the skin, but are largely ineffective in doing so.

In order for professional massage, sports or physical therapists to be most effective, they must be very physically fit, as to provide an effective deep tissue massage requires exerting great forces for long periods of time. Additionally, professionals must provide a series of deep tissue massages in succession, which requires even greater physical stamina, that frequently result in repetitive stress or other injuries to the professional.

In using conventional devices and methods for deep tissue massage, it has been found inconvenient, for example, that in an effort to penetrate severe muscle spasms, even professional therapists can inflict pain, or cause bruising to the skin in an effort to penetrate a severe or deep muscle spasm. Motorized massage devices typically have had a contact surface arrangement including a composition of rigid plastic or terry cloth in direct contact with a patient's skin which during operation of the device can result in chafing, abrasion, or bruising of the massaged skin or tissue. Terry cloth or a similar pad cover can be prone to disintegrate into airborne particles, which when breathed in, cause respiratory complications to the sinuses, throats and lungs in both the therapist and the patient.

Lastly, the operation of conventional massage devices typically is adjusted after a user provides a verbal or manual feedback signal to the operator of the device to adjust the device operation. For example, a user may lean forward to signal her desire for a less forceful massage therapy, or the user may stand up to signal her desire to end a massage treatment. These types of feedback signals corresponding to an operation of a massage device can be untimely and inefficient, possibly resulting in needless pain and discomfort endured by a user patient due to a delay or miscommunication of feedback regarding effects on the user's body from the massage device while in use.

BRIEF SUMMARY

According to an embodiment of the present disclosure, a motorized therapeutic massage device is disclosed. The device includes a motor, whether powered by electrical signals, by air, or by another fluid, the motor having a motor drive shaft, disposed within an enclosure; and a contact surface arrangement coupled to said motor drive shaft, by means of a transfer member disposed within an enclosure, that is offset from the center axis of the motor drive shaft and a center axis of the contact surface arrangement; and wherein the motor and driveshaft are coupled to drive the contact surface arrangement to impart both random orbital oscillating motion and percussive motion to the contact surface arrangement; and further wherein the contact surface arrangement creates a penetrating shockwave subcutaneously through human or animal muscle tissue, and minimizes the frictional engagement of skin or garments covering the skin, and minimizes temperature increase of the contact surface arrangement and the skin resulting from the frictional engagement.

In an embodiment of the present disclosure, a method of applying mechanical oscillating energy through human or animal muscle tissue comprises: contacting an area of skin covering human or animal muscle tissue, with a contact surface arrangement of a mechanical oscillation treatment device and applying power to a motor of said device while said contact surface arrangement is in contact with the area of human or animal tissue to apply random orbital oscillating energy to the tissue by oscillating the contact surface arrangement in a direction approximately parallel to a surface of the tissue in a random orbital motion having a variable orbit diameter to induce shearing and stretching forces in the tissue.

In an embodiment of the present disclosure, a method of applying mechanical oscillating energy through human or animal muscle tissue comprises: contacting an area of skin covered human or animal muscle tissue, with a contact surface arrangement of a mechanical oscillation treatment device and applying power to a motor of said device while said contact surface arrangement is in contact with the area of human or animal tissue to apply orbital oscillating energy to the tissue by oscillating the contact surface arrangement in a direction approximately perpendicular to a surface of the tissue in a random orbital motion having a variable orbit diameter to induce shearing and stretching forces in the tissue.

In an embodiment of the present disclosure, a method of applying mechanical oscillating energy through human or animal muscle tissue comprises: contacting an area of skin covered human or animal muscle tissue having muscle tension or soreness, with a contact surface arrangement of a mechanical oscillation treatment device and applying power to a motor of said device while said contact surface arrangement is in contact with the area of human or animal tissue to apply orbital oscillating energy to the tissue by oscillating the contact surface arrangement in a direction having both parallel and perpendicular components to a surface of the tissue in a random orbital motion to induce shearing and stretching forces in the tissue.

BRIEF DESCRIPTION OF THE DRAWINGS

The accompanying figures, in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which:

FIG. 4A is a perspective view of the motorized therapeutic massage device of FIG. 1 applying both random orbital and percussive forces to the skin at an oblique angle;

DETAILED DESCRIPTION

Introduction

Figure 1:
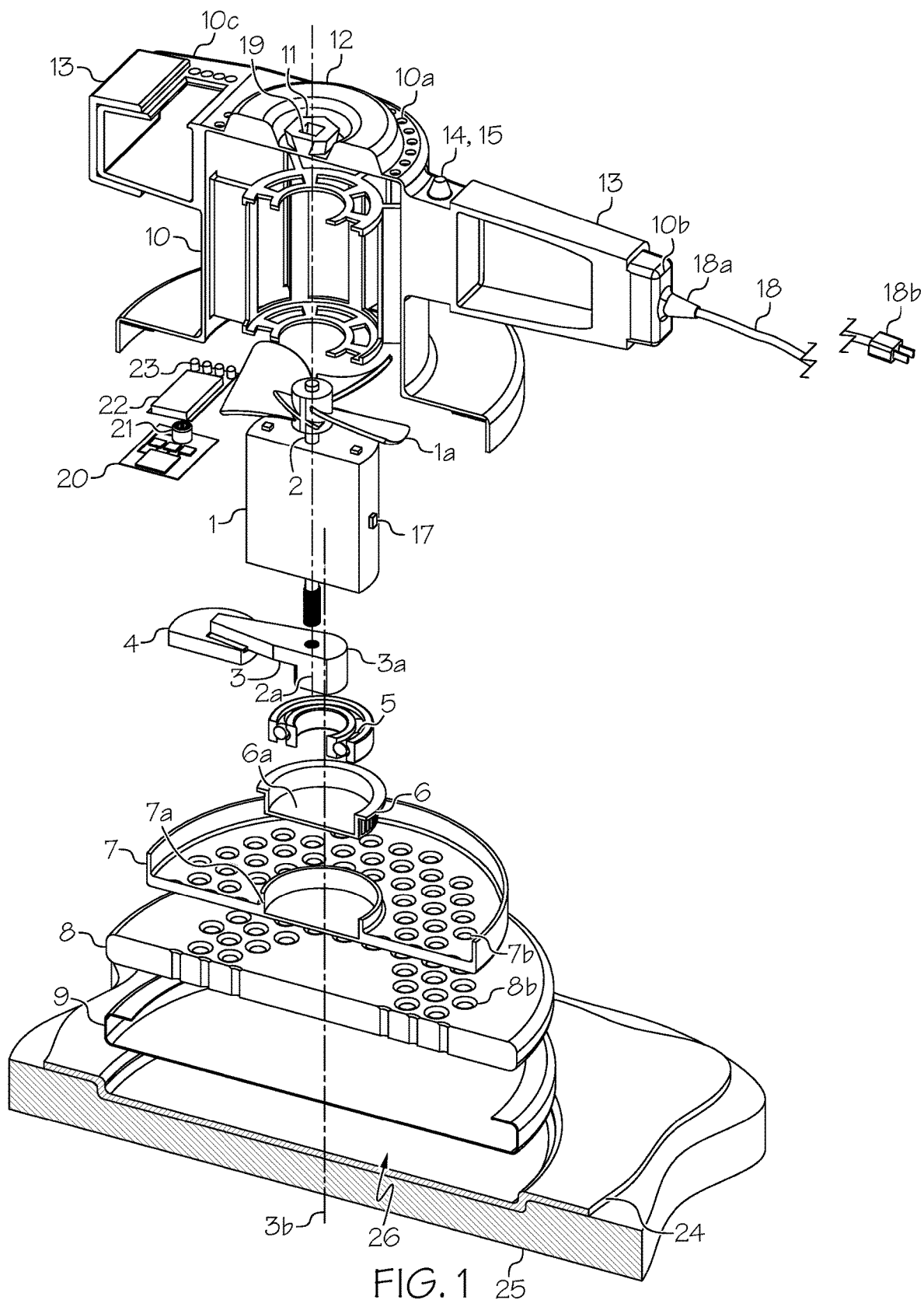
FIG. 1 is an exploded view of a motorized therapeutic massage device, according to one embodiment of the present disclosure.

Various detailed embodiments are disclosed herein. However, the various disclosed embodiments are merely examples, which can be embodied in various different forms. Therefore, specific structural and functional details disclosed herein are not to be interpreted as limiting, but merely as a basis for the claims and as a representative basis for teaching one of ordinary skill in the art to variously employ the present disclosure in virtually any appropriately detailed structure. Further, the terms and phrases used herein are not intended to be limiting; but rather, to provide an understandable description of the various detailed embodiments. Also, the terminology used herein is for the purpose of illustration and description by example and not of limitation.

Various embodiments of the invention can reduce massage therapy treatment to a small number of sessions, possibly of less than a single hour each, providing a very recuperative and effective deep tissue massage to a patient.

According to an example embodiment, a motorized massage device is provided with a contact surface arrangement having a low coefficient of friction. Previous motorized massage devices typically had an oscillating contact surface directly contacting a patient's skin where the contact surface included a composition of rigid plastic or terry cloth that can result in chafing, abrasion, or bruising of the massaged skin or tissue. Additionally, terry cloth or a similar pad cover is prone to disintegrate into airborne particles, which when breathed in, cause respiratory complications to the sinuses, throats and lungs in both the therapist and the patient.

According to an embodiment, a small, portable solution is provided as an alternative to using equipment that is difficult, if not impossible to transport to the user, or which may require the user to travel to the equipment. It is much more practical to employ the use of a small, portable solution in a user's home, for example, than having the user travel to the massage therapy equipment to undertake numerous, less effective treatments.

One or more embodiments of the present invention provide an apparatus and method that improve over the prior art by:

providing a portable massage device that allows a user or a professional to treat himself or a patient in an office or at home;

providing a means for chiropractic physicians to relax his or her patients prior to providing adjustment(s);

providing a quickly detachable massage pad with a substantially smooth surface that minimizes the frictional engagement of the patients skin, and may be used thru a garment the patient is wearing over his skin, or upon bare skin;

providing a solid or perforated massage pad cover that when in use provides a further cooling effect to a contact surface arrangement of the massage device by drawing in cooling ambient air between the contact surface arrangement and the user's skin;

focusing on risks associated with chafing and burning of the skin, and with hair entanglement;

provide for a means to detect the pressure and temperature of the contact surface and display over limit pressure and temperature conditions;

providing a means to prevent objects such as hair and clothing from becoming entangled within the unit;

providing a means to bear down on a pressure pad disposed on the enclosure to achieve an even greater depth of massage, without causing pain or injury to the user or massage therapist;

providing a fan or compressed air port within the unit to cool the device and provide for a smaller, lighter, safer, more maneuverable and longer lasting product;

providing a means to attach accessories to the massage device to allow additional features and accessories to be used with the device; and providing additional safety features that are not found on existing products, so as to prevent injury to the users and damage to the apparatus. For example, various embodiments include one or more sensors that are monitored by a programmed computer and controller to automatically shut off, or to otherwise adjust, the operation of the motor, and accordingly the revolutions of the contact surface arrangement, due to, for example, 1) determination that patient's hair or clothes are entangled with the moving contact surface arrangement (e.g., by using contact pressure sensors to monitor contact pressures detected on external surface(s) of the contact surface arrangement), 2) the temperature of the contact surface arrangement may rise above a threshold and a determination to activate a temperature protection of the contact surface and a patient's skin surface (e.g., by using thermal sensor(s) such as IR detectors or cameras 54 or temperature sensor(s) 35 to monitor temperatures on surface(s) of the contact surface arrangement), 3) activation of a revolutions limiter that limits revolution speed of the contact surface arrangement, and 4) the pressure of the contact surface of the contact surface arrangement on the surface of the patient's skin is determined to exceed a threshold; and additionally can include pressure pad, grip pads, longer power cord, and a communication system to communicate patient safety conditions to a remote computer system to alert operation personnel of a possible safety concern with the operation of the massage device on a particular patient.

Various embodiments of the present system and method improve over the prior art by:

providing a means to mount the device to and communicate with a computer controlled, 5 axis CNC (computer numerically controlled) motorized machine;

providing a means to input relative coordinate data from, and to capture topographical data of the individual being treated and communicate it to the CNC motorized machine;

providing a means for patient and therapist to communicate, including but not limited to verbally, in a high noise environment when a patient is receiving treatment; and providing a means to store and communicate data including, but not limited to position, pad pressure, temperature, rate of rotation, rate of travel, run time etc.

Definitions

The following terms shown within quotation marks, whether capitalized or otherwise, when used in the present disclosure are defined as follows:

"Contact Surface": An outer surface of a Contact Surface Arrangement of a motorized therapeutic massage device, where the outer surface is configured for directly contacting a surface of a skin covered muscle tissue receiving a therapeutic massage with the motorized therapeutic massage device.

"Contact Surface Arrangement": A portion of a motorized therapeutic massage device that couples the "random orbital oscillating" motion, and the "percussive" motion, produced by the motor of the motorized therapeutic massage device, and their respective "random orbital oscillating" and "percussive" forces to a surface of a skin covered muscle tissue of a user. This portion of the device may include various different configurations of the following elements: a massage pad mounting plate and a Massage Pad, and which may optionally also include a massage pad cover.

"Massage Pad": A portion of the motorized therapeutic massage device that couples the "random orbital oscillating" motion, and the "percussive" motion produced by the motor of the motorized therapeutic massage device, and their respective "random orbital oscillating" and "percussive" forces to a user, whether human or animal, skin and tissue. Even though it is understood that the "massage pad" may not physically contact either Skin or Tissue, as defined below, it is understood that the "massage pad cover" does not inhibit any motion or forces, but acts to minimize the frictional engagement of the "massage pad" against the user, human or animal, Skin. As such, the "massage pad" and the "massage pad cover" may be individually or collectively used interchangeably, or also be referred to as being part of the "contact element" or "contact surface arrangement".

"Massage Pad Assembly: Generally used to describe the "massage pad" 8, the "massage pad mounting plate" 7, and the "massage pad cover" 9.

"Skin": Generally used to describe naked human skin. Also may include, but not be limited to the expanse of human skin, and the underlying "Tissue" disposed in proximity of the general area. Also may include the skin of animals, including but not limited to horses and cattle.

"Tissue": Generally used to describe human muscle tissue. Also may include, but not be limited to the skin, muscle fascia, tendons, cartilage, fat, blood vessels, lymphatic vessels, lymph nodes, internal organs, and animals.

"User": Generally used to describe a person operating the device. Also may include, but not be limited to a person using the machine on him or herself, or on another individual or an animal. Also may include, but not be limited to chiropractic physicians or massage, sports, or physical therapists, and a group or multiple groups of people. Also may include, but not be limited to, one user receiving treatment from another individual, therapist, trainer, rehabilitation tech, or physician, where that user may be also referred to as a "patient".

"Muscle Spasm": Generally used to describe a sudden, involuntary contraction of a muscle, a group of muscles, or a similarly sudden contraction of an orifice. Also may include, but not be limited to a muscle cramp which is often accompanied by a sudden burst of pain, or involuntary muscle contractions, which may be more serious, depending on the cause. Also may include, but not be limited to insufficient hydration, muscle overload, and absence of electrolytes. Spasmodic muscle contraction may be due to a large number of medical conditions, including, but not limited to dystonias, or hypertonic muscle spasms—a state of chronic, excessive tension in a resting muscle.

"Motor": Generally used to describe a motor powered by electrical power, or alternatively powered by pneumatic fluid pressure or hydraulic fluid pressure; and may include, but not be limited to, a DC motor, a reversible AC or DC motor, a stepper motor, or any motor that is well understood by those of ordinary skill.

"Massage Head": Generally comprised of a drive assembly and a massage pad assembly, such drive assembly having a motor shaft that delivers mechanical energy to a transfer member which is coupled to a quick disconnect part A that is mated with a quick disconnect part B, to which the massage pad assembly is coupled.

"End Effector": Generally used to describe a device that is rapidly attached/detached to/from a robotic arm via a standard (or custom designed) robotic arm connector.

Massage Head End Effector: Generally used to describe the aforementioned "Massage Head" when coupled to a robotic arm via a standard (or custom designed) robotic arm connector to transfer between the robotic arm and the massage head one or more of the following: electrical signals, power signal, compressed air, vacuum, or liquid fluid, or any combination thereof.

Accessory Mount: Generally used to describe a mechanical coupling to allow accessories to be detachably connected to the massage head, or the massage head end effector, to be detachably connected to other handles or fixtures in a number of mounting configurations. Such mounting configurations include, but are not limited to, those having electrical, data, control, or other connections, or a standard (or custom designed) robotic arm connector including but not limited to those defined by robot flange interface DIN ISO specifications.

Quick Disconnect Accessory Mount: See Accessory mount.

Description of Examples

Various embodiments of the present disclosure relate to an apparatus for use in therapeutic massage applications in which forces are provided to an outer surface of the human body and subcutaneously within human tissues. The apparatus, according to one example, includes a covered, motor driven pad that imparts both random orbital and percussive forces to the skin and tissue of a human body in various contact arrangements between a massage pad and the skin and its underlying tissue.

Figure 2:
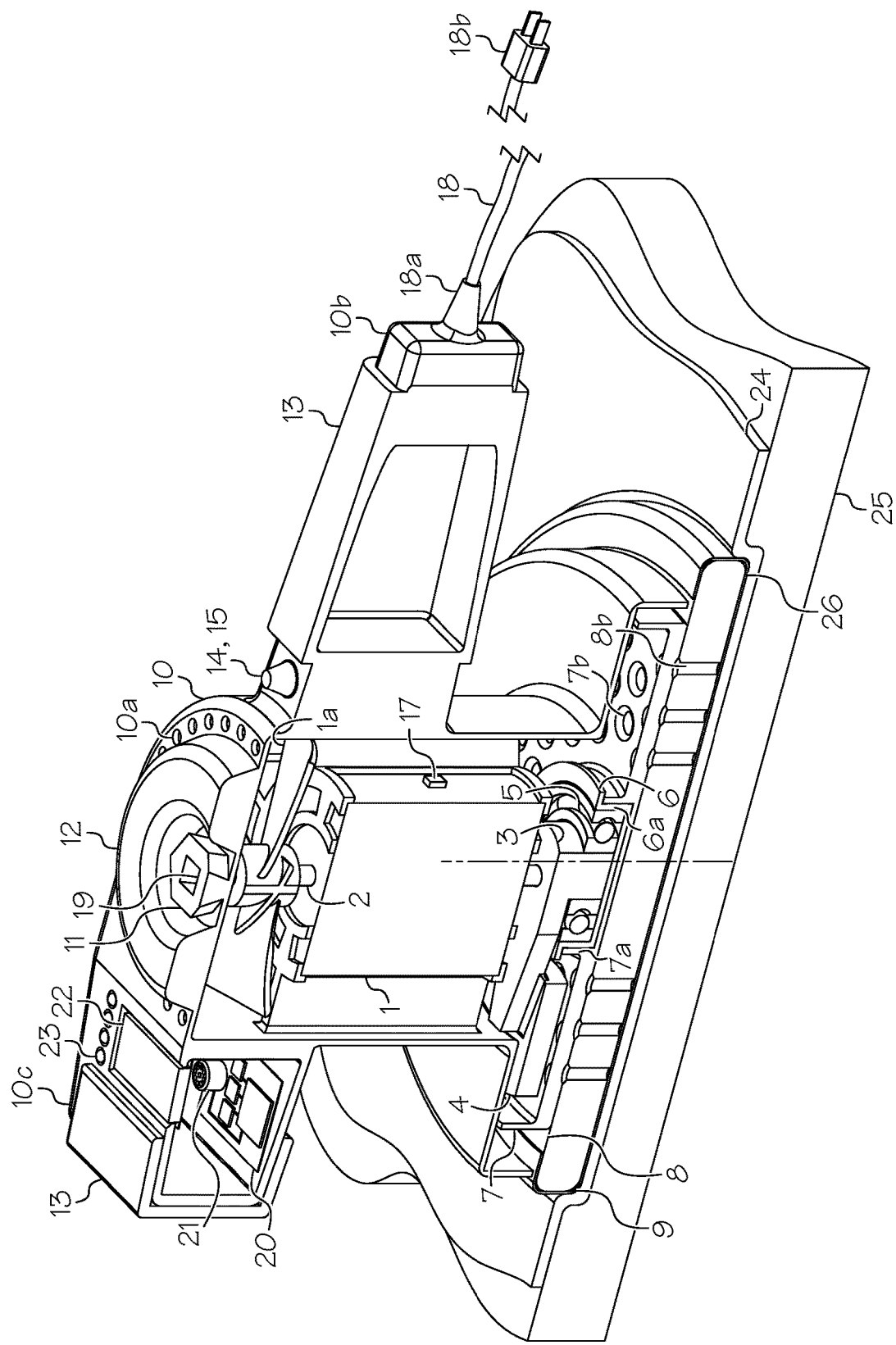
FIG. 2 is a cross sectional view of the motorized therapeutic massage device of FIG. 1.

Referring now more particularly to FIGS. 1 and 2, FIG. 1 shows an exploded view of one example embodiment of a portable, hand held, motorized therapeutic massage device and FIG. 2 shows a cross-section thereof. An electrical or compressed air powered motor 1 has a cooling fan 1a and a motor drive shaft 2 that delivers mechanical energy to a transfer member 3 having an offset hub 3a with center axis 3b. The transfer member 3 has a counter weight 4 and the offset hub 3a within an inner bearing race of a ball bearing assembly 5, also consisting of ball bearings and an outer bearing race which couple to quick disconnect mounting plate 6. A contact surface 8, 9, according to the present example, is coupled to the transfer member 3 by the offset hub 3a and has a center axis coincident with the center axis 3b of the offset hub 3a. The contact surface 8, 9, is coupled to the motor drive shaft 2 by means of the transfer member 3. The center axis 3b of the offset hub 3a and the center axis of the contact surface 8, 9 are offset from the center axis 2a of the motor drive shaft 2. The contact surface 8, 9, in the example, comprises a multilayered component including, but not limited to a layer of cellular foam or rubber, and a covering substantially including, but not limited to leather or woven cloth and vinyl, either solid or perforated. The quick disconnect mounting plate 6 has a quick disconnect part A 6a, that mates with quick disconnect part B 7a, disposed on a massage pad mounting plate (or rigid disk) 7. According to various embodiments, a plurality of sensors in the motorized therapeutic massage device can measure at least one state of properties associated with the contact surface 8, 9, including, but not limited to temperature (see, for example, temperature sensor 8c in FIG. 1) or pressure (sensor not shown). According to certain embodiments, the plurality of sensors is coupled to an indicator or indicators in the motorized therapeutic massage device. A shutoff, according to these embodiments, is configured to be activated when one or more of the plurality of sensors exceeds a pre-set value.

According to this embodiment, the quick disconnect feature is shown as one example, and is not intended to limit other possible configurations, including, but not limited to reversing the motor 1, or having a lock, a detent, a turret or other style of chuck. A massage pad 8 is disposed adjacent to the massage pad mounting plate (or rigid disk) 7. The massage pad 8 may be composed of one or more materials, including but not limited to, cellular foam or rubber, expanded polyurethane, cellular rubber or a semi-rigid foam. Vent holes 7b and 8b provided in the massage pad mounting plate 7 and the massage pad 8 respectively, allow air from the top of the unit to move through the enclosure air vents 10a, such as by the cooling fan 1a or by another air movement device, including but not limited to compressed air to cool the motor 1, or for other purposes, or a fluid transferred through the robotic quick disconnect mount 11 to cool components within the massage head system 40, including but not limited to the motor, the massage pad 8 and the massage pad cover 9. According to various embodiments, air or water, or a fluid transferred through air/fluid couplers 11g and 11h and via air/fluid line(s) 11i (all shown in FIG. 10), the robotic quick disconnect mount 11 can provide pneumatic fluid pressure or hydraulic fluid pressure to cool and/or power the motor. Gripping the primary handle 10b and the secondary handle 10c, where in this example the secondary handle 10c has safety grip pads 13, the user can direct position the enclosure 10, so as to couple the force from the massage pad 8 thru the massage pad cover 9, the patients' garments (not shown), the patient's skin 24, and into the patient's muscle tissue 25. A pressure pad 12 disposed on the enclosure provides a means to bear down on to achieve an even greater depth of massage, without causing pain or injury to the user or massage therapist.

In a first arrangement, referring to FIGS. 1 and 2, for example, and not for limitation, the large surface area of the pad 8 parallel to the body of the patient is shown contacting the skin surface of the patient and providing shearing and stretching random orbital motion across the skin, while pressed into the patient's tissue with the large flat portion of the massage pad 8 and the massage pad cover 9 pressed into the muscle tissue 25. In this position, the flat portion of the massage pad 8 will impart a random orbital oscillating motion (i.e., the random orbital oscillating motion having a variable orbit diameter) to the skin 24 that it is in contact with, and the muscle tissue 25 that it is pressed into. Mainly friction force between the lateral pad surface and the skin surface at the contact area transfers lateral vibratory vibration from the pad 8 to the skin of the patient. With every rotation of the massage pad 8, shearing and stretching forces are coupled into the muscle tissue 25. In one example embodiment, the massage pad cover 9 is constructed of a flexible covering of one or more layers, and includes but is not limited to one or more materials such as leather, Teflon, woven cloth, vinyl, perforated leather, perforated Teflon, perforated woven cloth, or perforated vinyl. In the example, the massage pad cover 9 is shown including non-perforated material.

Continuing with the example, in a second arrangement, an edge surface (i.e., other than the large flat portion) of the pad 8 contacting the skin 24 provides deep pulsating vibrations into the skin surface typically at a normal or near normal axis with the skin surface.

With reference to FIGS. 1, 2, 4, and 4A, an exploded view, a cross-sectional view, and 2 perspective views, of an example embodiment of a motorized therapeutic massage device are shown, for example, and not for limitation, illustrating the interface of the mechanically engaged human skin and its associated human tissue, with the massage pad cover when pressed into an expanse of the human skin and tissue.

Analysis using a stroboscopic light source has shown that this force propagates approximately 6 inches through the muscle tissue, and is visible as ripples in a wave. Because the human body is composed mostly of water, this should not be a surprise.

In physics, the phenomenon of resonant frequency will show that based on the density of the muscle tissue 25, there will be a preferred oscillating motion revolutions per minute (RPM) that will propagate a wave further than all other RPMs.

As an example, if a professional football player were suffering from a pulled thigh muscle, any exertion on the muscle would cause the muscle to contract into a muscle spasm. This is the body's self-defense method, in which the thigh muscle is being contracted to prevent a more serious injury such as a muscle tear. The football player could loosen up the thigh muscle using a consumer version at his home, several times a day, largely by using the motorized therapeutic massage device in a random orbital oscillating force. The force on the muscle would cause delivery of compounds including but not limited to oxygen, blood and lymphatic fluids through the vessels and tissues, healing the injury and reducing swelling, and flushing toxins including but not limited to lactic acid out of the muscle tissue. This increased blood flow as a result of friction generated warmth would subsequently further warm the area, opening a pathway to cause blood vessels to stay dilated longer, thus helping the football player's body, in this example, to continue healing itself. As the muscle spasm eases, the player would be able to better tolerate a more aggressive percussive force, able to penetrate deeper into the tender muscle, and continued therapy thru a sports rehab trainer, to enable the player to play for a game that he would otherwise not be able to play.

By promoting the circulation of substances in the body, many medical conditions can be improved. Patients having heart disease, diabetes, phlebitis, for example, and other illnesses resulting in compromised circulation of fluids including but not limited to blood and lymphatic fluid, and congestion within lungs and tissues would be benefited by the use of such therapy. The improvement of circulation would cause congested blood vessels and tissues to be flooded with oxygen, and waste products or toxins including but not limited to lactic acid to be flushed from the tissues and lymphatic vessels. An example of this would be forcing the blood from one's calves upwards towards the heart to prevent edema in the legs. The resulting reduction in swelling in the calves would allow increased flow of blood to continue to flush the calve muscles with blood, thereby opening up a pathway for the body to allow the circulation of blood and lymphatic fluids to continue to nourish and flush tissues that would otherwise fail to be nourished and flushed as effectively.

An embodiment of the disclosure is further related to massage devices used to reduce muscle spasms, by both warming up muscle tissues both prior to physical activity, and relaxing muscle tissues after physical activity. Muscle spasms that are so deep within large muscle tissues may be impossible to be treated using conventional massage therapy. The prior art discloses numerous massage devices and methods that have been used to treat muscles, muscle spasms, improve circulation, promote the flushing of waste products from tissues, and break up bronchial secretions, using massaging circular oscillations across the skin and tissue and alternatively percussive types of force directed generally normal to and into the skin and tissue.

Many prior art vibrators and massage devices require massage directly to the skin, and as such, are not effective for prolonged use, as chafing or burning of the skin can result. Many of these devices and treatments pose the risk of hair or clothes entanglement, and therefore require the patient not be clothed. Additionally, prior art devices are prone to overheating, forcing the user to wait between uses, to allow the device to cool down, or otherwise risk burning out the device, thereby requiring the device to be repaired or replaced. Compressed air power tools provide an excess of cold air. Regulating the flow of such compressed air will provide a perfect solution to the problem of heat dissipation.

Referring again especially to FIG. 1, in the present example, AC power is provided to the motor 1 by a power cord 18, having both a plug 18b and a strain relief 18a. The AC power is switched by power switch 14 and the motor 1 is allowed to run at variable speeds by means of variable speed control 15, which in this embodiment, by example is incorporated into power switch 14, and includes, but is not limited to, a rheostat, a solid state controller, or a multi-position switch. Additionally, other aspects may include but not be limited to a high temperature fault shutting off the motor 1 when motor temp sensor/shutoff 17 indicates the motor 1 is overheating, or RPM sensor/rev limiter 16, indicates and prevents excessive RPM of the massage pad 8, for example, if the operator lifts the contact surface of the contact surface arrangement away from a patient's body part being treated. An embodiment of the device can provide a means to cool the massage pad 8 by any one or more, but not limited to, the vent holes 7b and 8b and arrangement that has already been discussed above, a Peltier solid state cooling chip, or a secondary Fan, compressed air or the like, or any combination thereof. Still another example embodiment of the device includes means to power the device by a quick disconnect battery pack.

Controller board 20 comprises a microcontroller and its associated support electronics, and according to the present example including, but not limited to, an Arduino, Stamp or Electric Imp microcontroller, memory chips, power supply, interface circuitry, motor controller and other circuitry including but not limited to circuits for wired or wireless communication from the microcontroller to other devices, including but not limited to cellular networks, wired (Ethernet) or wireless (Wife) networking, wired USB, or wireless Bluetooth, BTLE (Bluetooth Low Energy), or NFC (Near Field Communication) circuitry, all of which are well known by those skilled in these arts.

According to the present example, a plurality of sensors including but not limited to sensors for measuring temperatures, pressures and motor torque or speed or sensors for detecting and communicating device position and orientation such as digital gyroscope, magnetometer, and accelerometer chips, can be coupled to the microprocessor and its associated circuitry. Additional programmed features of the microcontroller, according to the example, include but are not limited to such aforementioned high temperature protection 17, which would shut off motor 1 if overheating, or limit RPM via a rev limiter 16, and display an error condition via one or more visual indicator 23 or visual display 22. The microcontroller is programmed to capture and store data from the plurality of sensors, determine load upon the motor, and provide alerts when pre-programmed set points are exceeded. Alerts include but are not limited to triggering visual and/or audio indicators, communication via a wired or wireless connection or via an email alert, via the video display 22, one or more visual indicator(s) 23, audible indicator 21, such as a piezoelectric transducer. Technologies include but are not limited to microprocessors and their associated support circuitry, sensor and programming technology and indicators, and wired and wireless connection technologies, which are well known by those skilled in the art. Valuable logged data would allow engineering to better determine in field product use and to fine tune design improvements for improved customer service, a greater degree of reliability, and extended product life.

FIGS. 1 and 2 show accessory mount 11, which allows accessories to be attached to the device unit for other purposes, or the unit to be attached for other purposes, including, but not limited to mounting to a massage chair, a fixed wall mount, a dynamic wall mounted actuator, or on a robotically controlled system 50.

Such robotically controlled system may include but not be limited to a system consisting of a multi-axis gantry style X-Y table or a robot arm (Cartesian), 6-Axis (or more), or SCARA style robotic system, video cameras, laser, lidar or ultrasonic rangefinders for object detection or a laser scanner to topographically map the contours of a patient's body. Integration of all sensors and functions of the robot includes, but is not limited to freely available OS (Operating System) software such as Microsoft Robot Development System (MSRDS) or the Open Source Linux based Robot Operating System (ROS) to integrate all functions of the robot. One skilled in the art could integrate the massage head unit (e.g., multi-axis control head), robotic arm, robotic OS software, a plurality of sensors, such that the system will elevate to safely detect and perform far more effective massages than those found in the prior art systems and devices.

Figure 3:
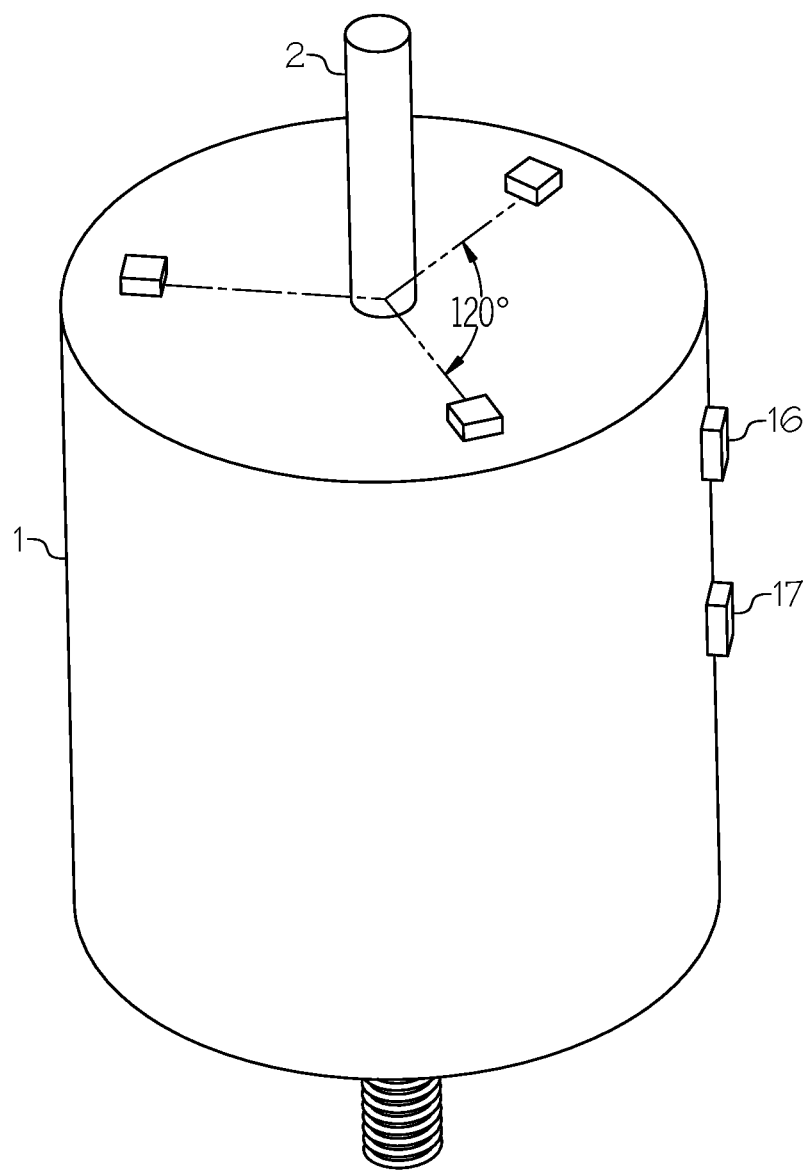
FIG. 3 is a perspective view of a motor of the therapeutic massage device of FIG. 1, showing one embodiment of the pressure and temperature sensors.

FIG. 3 is a perspective view of a motor of the therapeutic massage device of FIG. 1, showing one embodiment of RPM Rev Limiter 16 and motor temp sensor/shutoff 17.

Figure 4:
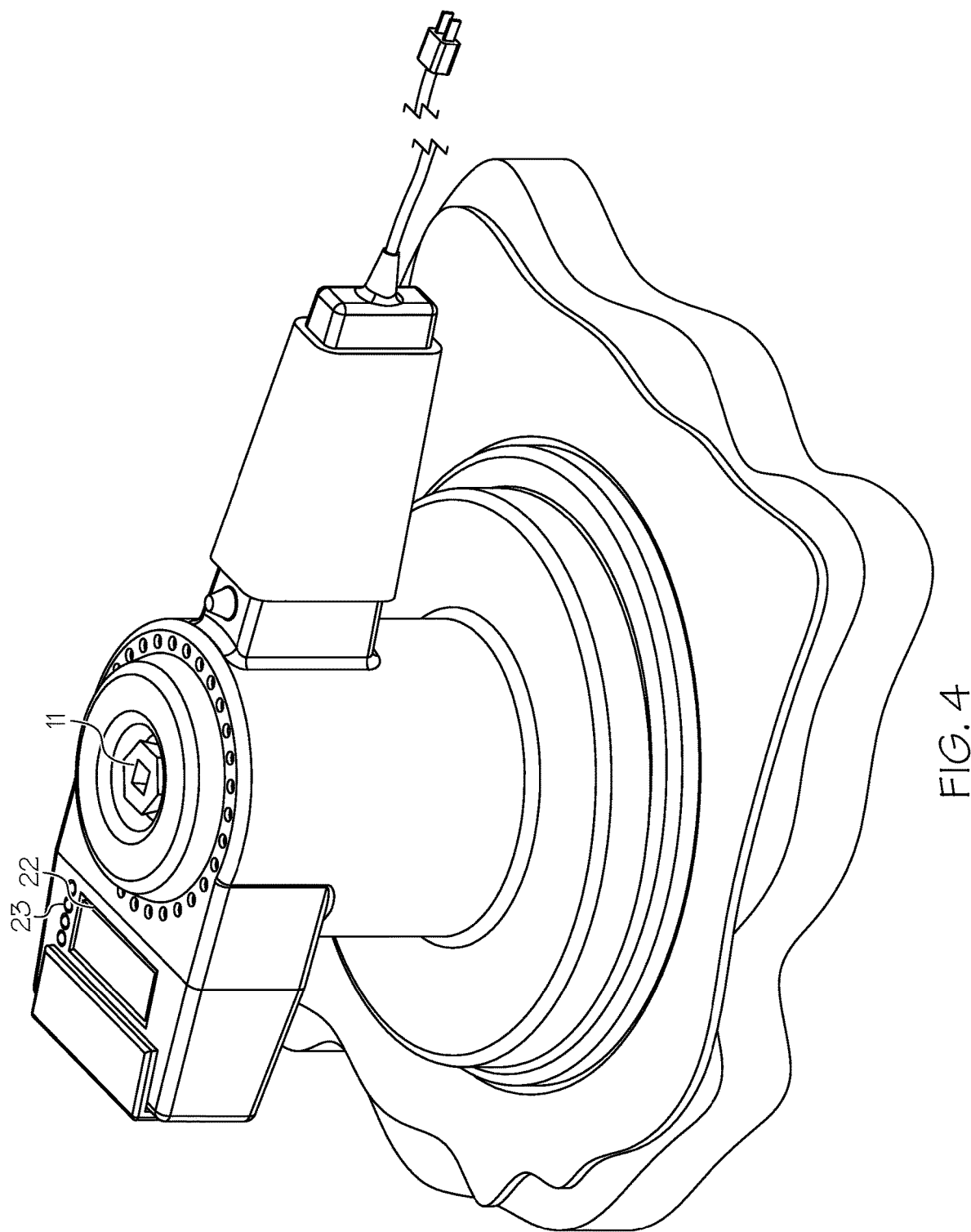
FIG. 4 is a perspective view of the motorized therapeutic massage device of FIG. 1, applying both random orbital and percussive forces to the skin at a normal angle to the skin.

FIG. 4 is a perspective view of a portable hand held motorized therapeutic massage device having visual indicators, a visual display, and accessory mount 11. FIG. 4 illustrates only one example embodiment of an accessory mount, and it is not intended to limit the scope of an accessory mount.

FIG. 4A is a perspective view of the example motorized therapeutic massage device of FIG. 1 applying both random orbital and percussive forces to the skin at an oblique angle. FIG. 4A clearly illustrates the interface 26 between the massage pad 8 of the therapeutic massage device and the skin 24 of the user.

Figure 5:
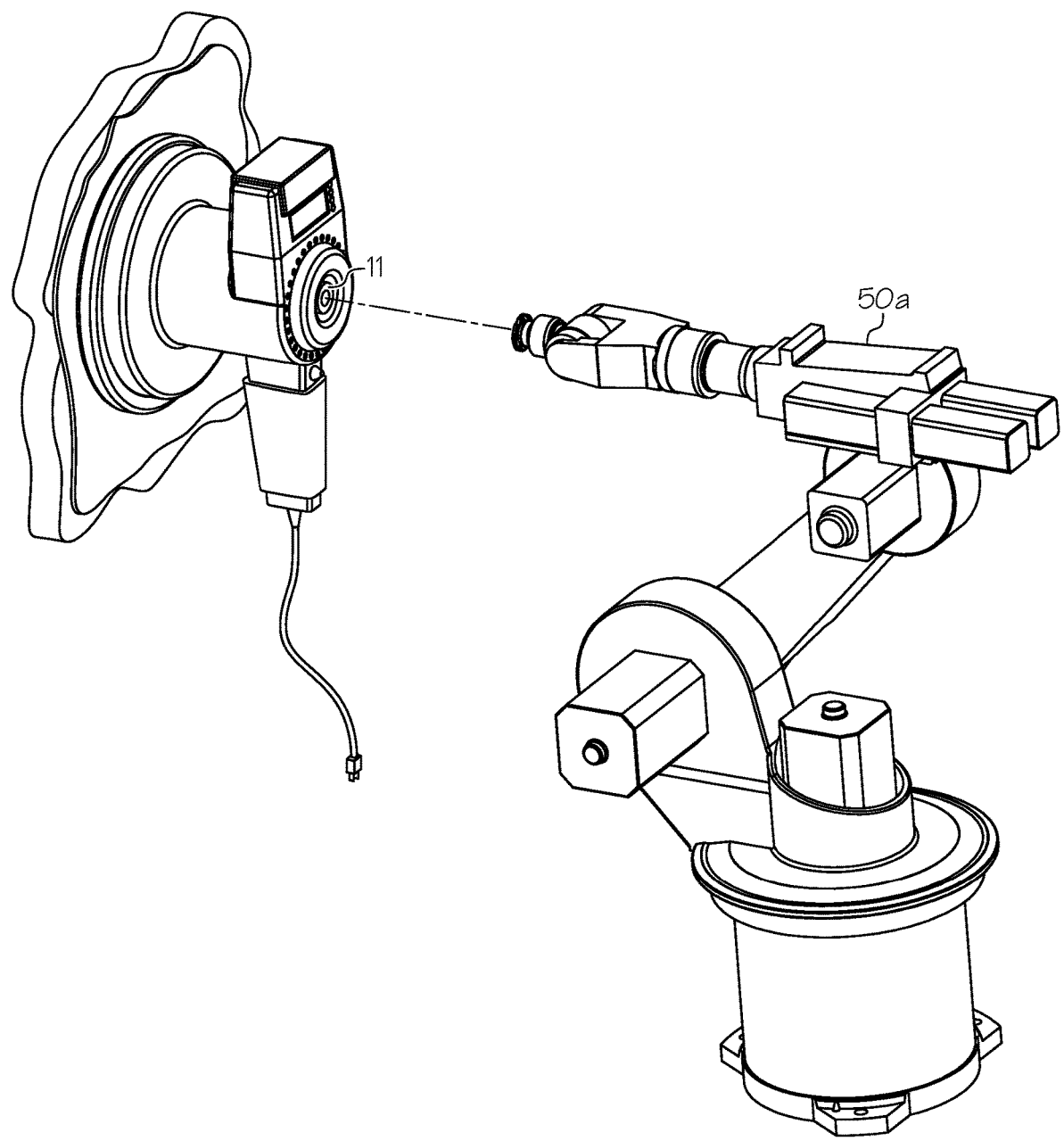
FIG. 5 is a perspective view of the motorized therapeutic massage device exploded from the robotic arm of a robotic system.

FIG. 5 is a perspective view of the accessory mount 11 of the motorized therapeutic massage device exploded from the mate of accessory mount 11 disposed on the robotic arm 50a of a robotic system.

Figure 5A:
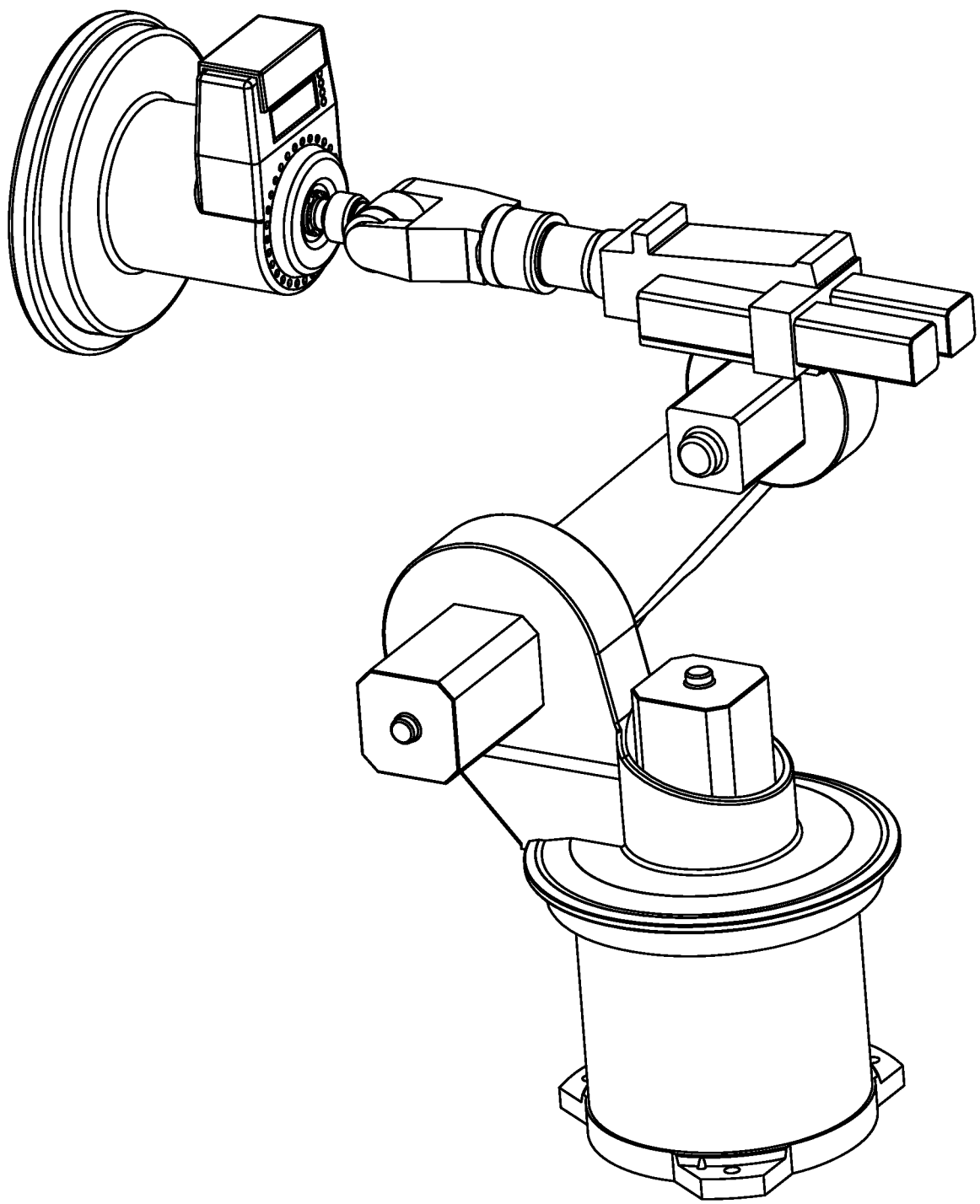
FIG. 5A is a perspective view of the motorized therapeutic massage device attached to the robotic arm of a robotic system.

FIG. 5A is a perspective view of the motorized therapeutic massage device disposed upon the robotic arm of a robotic system.

Figure 5B:
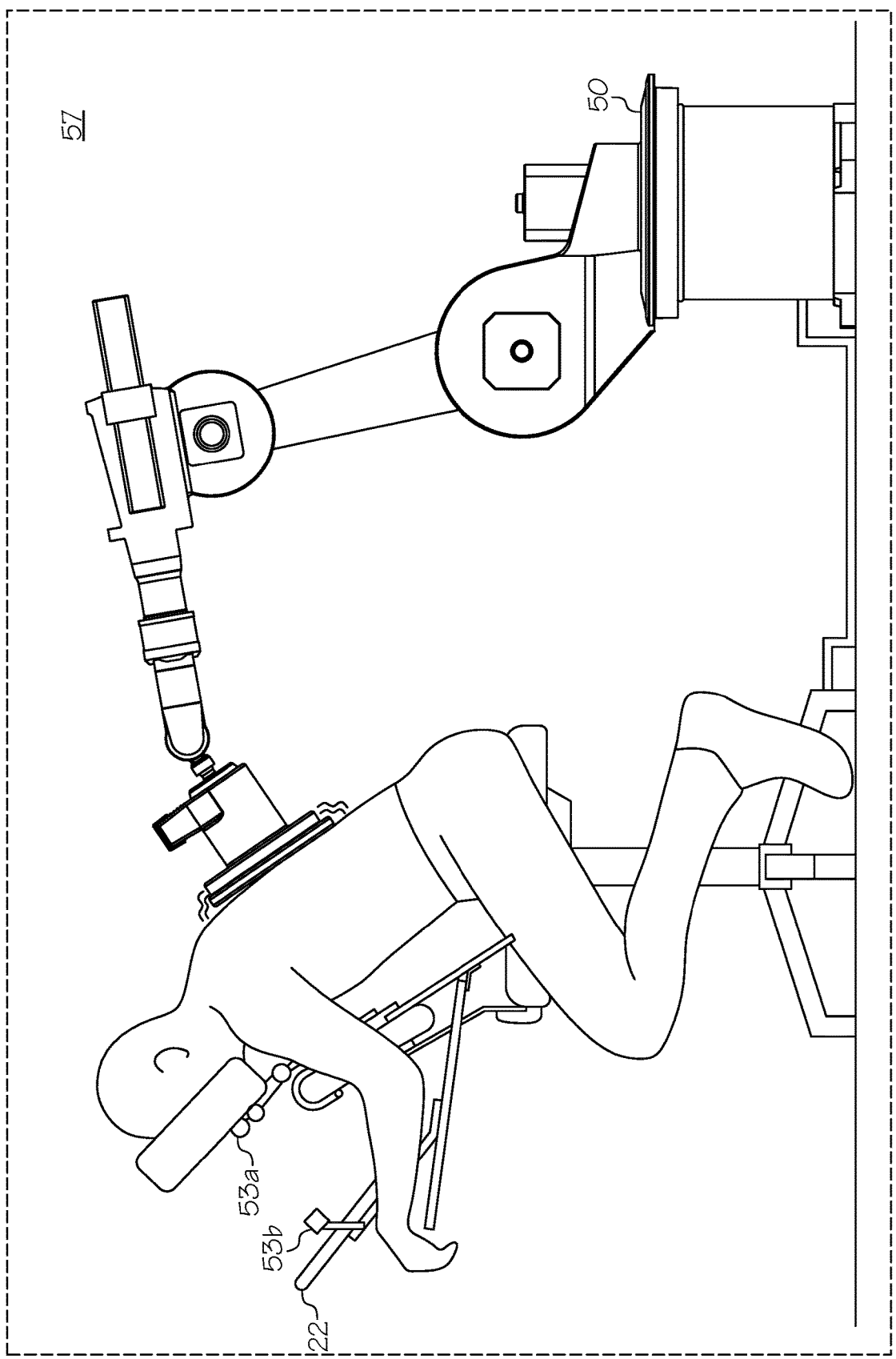
FIG. 5B is a view of a user receiving a massage therapy treatment via a deep tissue massager disposed upon the robotic arm of a robotic system.

FIG. 5B is a view of a user receiving a massage therapy treatment via a deep tissue massager disposed upon the robotic arm of a robotic system. The user, while seated upon a massage chair, views a visual display 22 that provides the user with functional control of the robotic controlled massager system 50, and speaks into user interface microphone 53a, as camera 53b documents his massage therapy treatment, user interfaces 53a and 53b being communicatively coupled to robotic controlled massager system 50.

Figure 6:
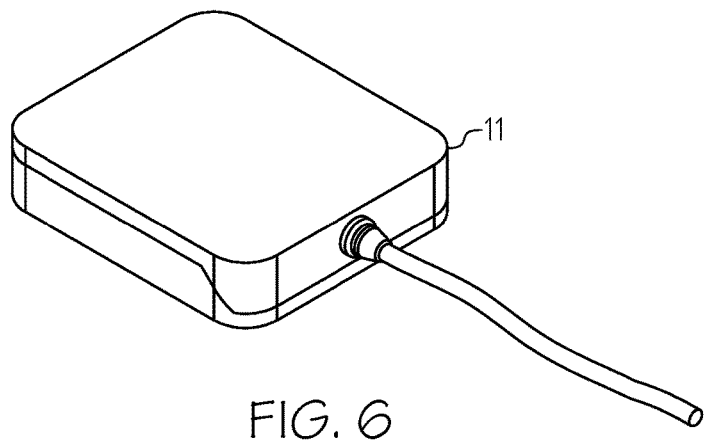
FIGS. 6, 6A, 6B, are a set of perspective views of a quick disconnect mount to couple power and data, and to mechanically couple the massage device to a mounting fixture, handle or accessory.
Figure 6A:
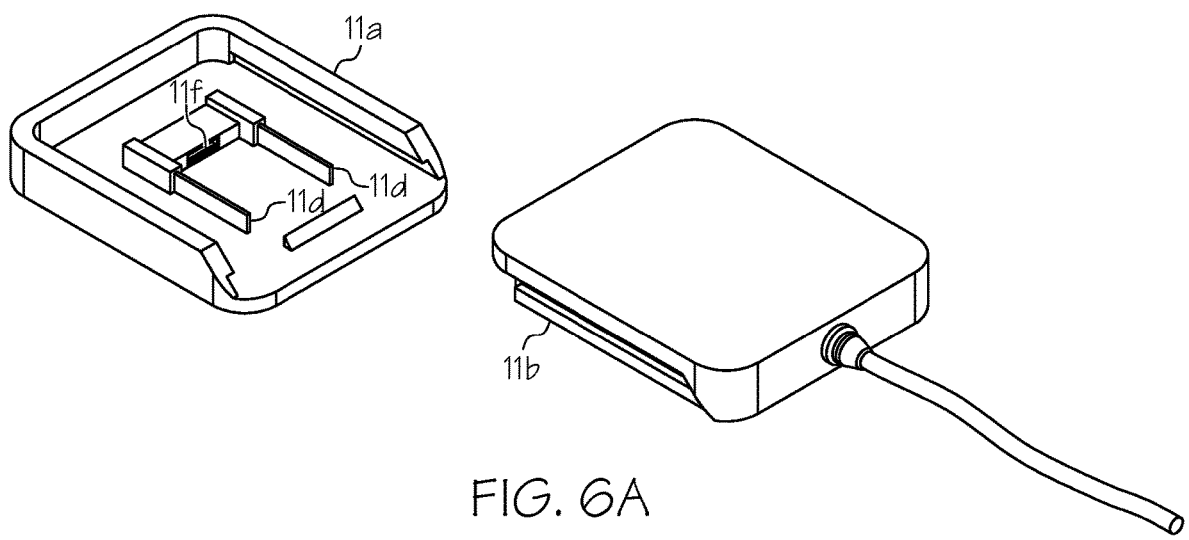
Figure 6B:
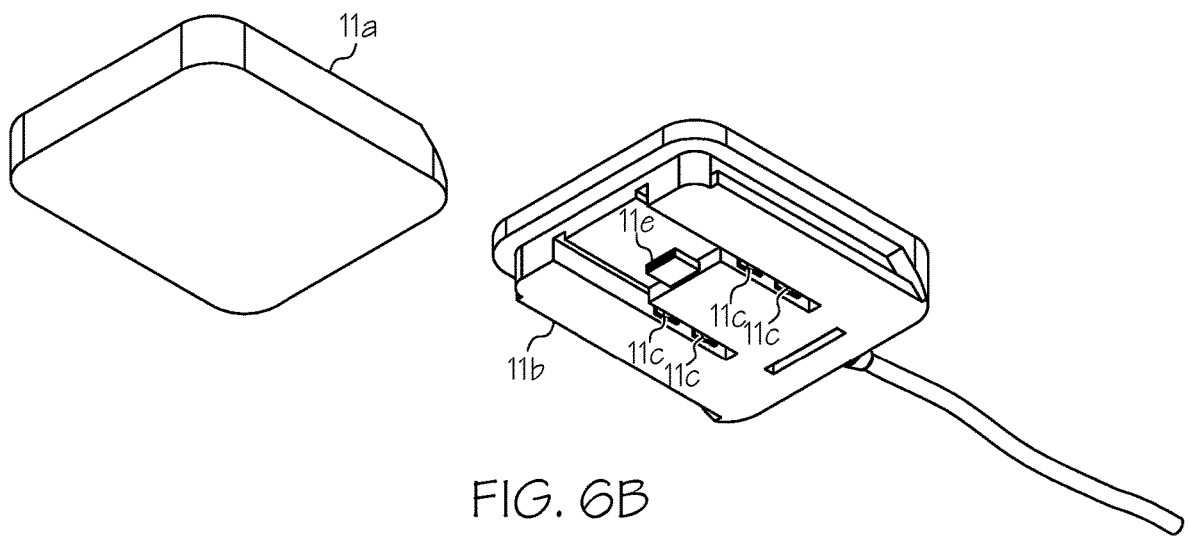

FIGS. 6, 6A, and 6B, are a set of perspective view drawings of a quick disconnect accessory mount 11 to couple power and data, and to mechanically couple the massage device to a robotic arm of a robotic system. The quick disconnect mount of these drawings consisting of two halves, massage head adapter accessory mount 11a and power adapter accessory mount 11b. This pair of accessory mounts enables a user to mount one massage head system 40 selected from a plurality of mount compatible massage head systems 40 with mount compatible fixtures, accessories, or handle configurations. In addition to mechanical coupling, this pair of adapters also couples power, data signals, and control signals. This enables a user to upgrade or adapt one or more massage heads in numerous configurations by attached it to a plurality of handles or fixtures. These drawings illustrate only one example embodiment of a quick disconnect accessory mount 11, and it is not intended to limit the scope of an accessory mount. The quick disconnect accessory mount 11 is intended to be the cornerstone of a plurality of static, moveable and powered mounting fixtures, swappable handle styles, and accessories. FIG. 6A is an exploded view of the two halves of the accessory mount adapters, massage head 11a and power adapter 11b viewed from above, showing electrical power connector 11d and electrical data connector 11f, and FIG. 6B is an exploded view of the two halves of the accessory mount adapters, massage head 11a and power adapter 11b viewed from below showing electrical power connector 11c and electrical data connector 11e.

Figure 6C:
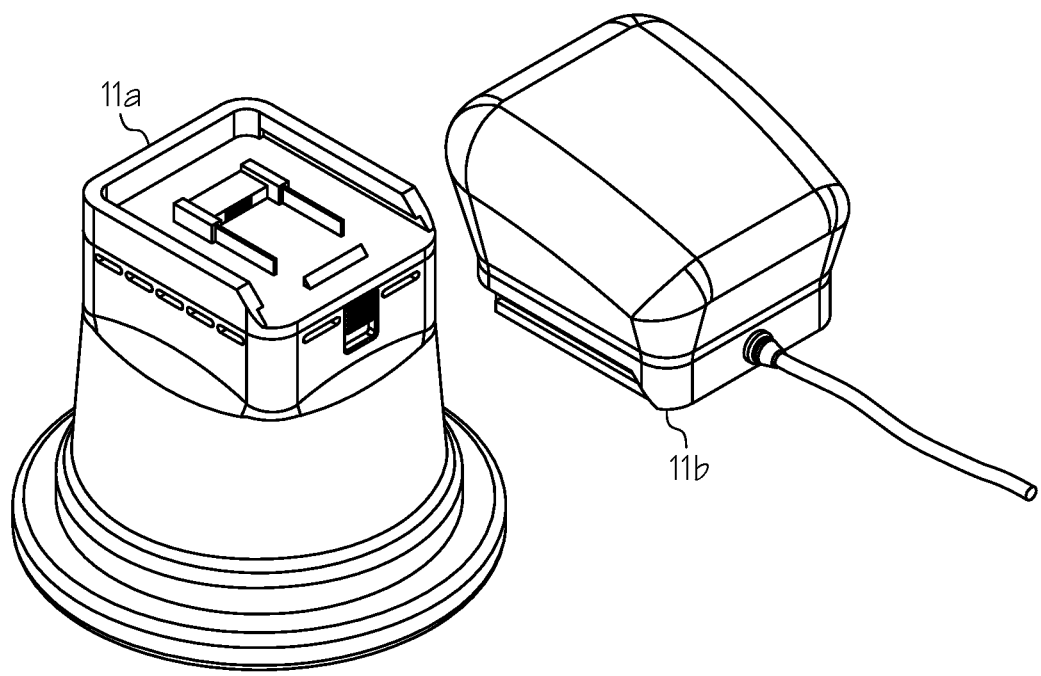
FIGS. 6C and 6D are views of a handheld massage head having a quick disconnect accessory mount configured to mate with a palm grip style power handle to couple power and data, and to mechanically couple a massage head to a palm grip style power handle.
Figure 6D:
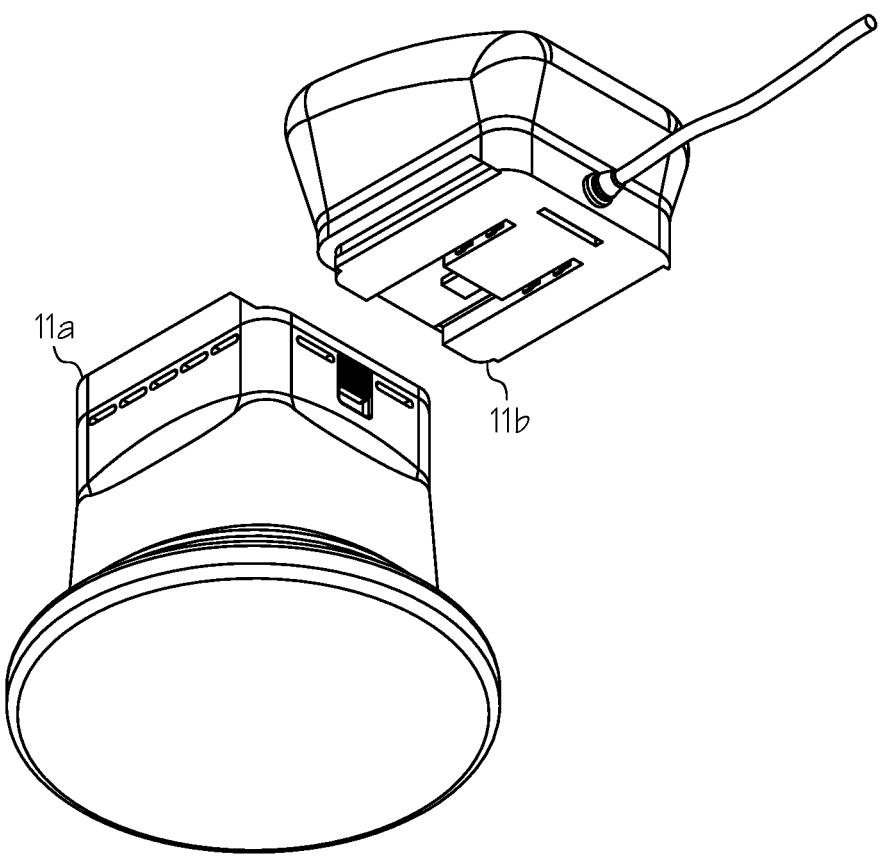

FIGS. 6C and 6D are perspective views of a handheld massage head having a massage head adapter accessory mount 11a, exploded from a palm grip style power handle having a power adapter accessory mount 11b to couple power and data, and to mechanically couple a massage head to a palm grip style power handle. FIG. 6C is a view of the two halves of the accessory mount enabled palm grip and massage head system 40 exploded away from each other, viewed from above. FIG. 6D is a view of the two halves of the accessory mount enabled palm grip and massage head system 40 exploded away from each other, viewed from below.

Figure 7A:
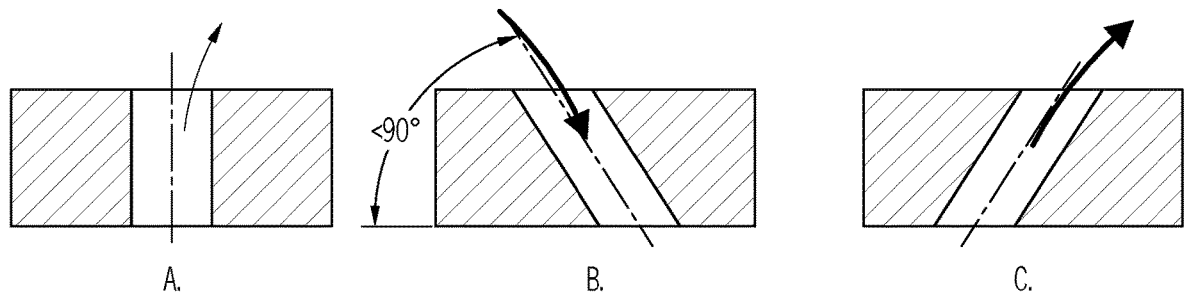
FIG. 7A is a cross sectional view comparing airflow thru orthogonal vent holes to airflow thru oblique vent holes.

FIG. 7A is a cross sectional view comparing airflow thru orthogonal vent holes to airflow thru oblique vent holes. Increased airflow thru oblique vent hole styles B and C is represented with a heavier weight arrow compared to the decreased airflow thru orthogonal vents. FIG. 7A is a representation of cross sectional views of a plurality of styles of air vents to promote airflow thru the massage pad assembly 40b. FIG. 7A, Sketch A represents an orthogonal vent having a limited volume of air passing thru it, whereas sketch B represents an vent angled inward towards the direction of rotation of the massage pad, relative to the orthogonal vent shown in Sketch A (having an angle of less than 90 degree). This angled vent provides a greater volume of airflow (represented by a heavier arrow) downward into the vent. Sketch C represents a vent angled in the opposite direction, (having an angle greater than 90 degrees), which encourages airflow in the opposite direction, out of the vent (the opposite angle direction from sketch B, but still having enhanced airflow volume compared to Sketch A.

Figure 7B:
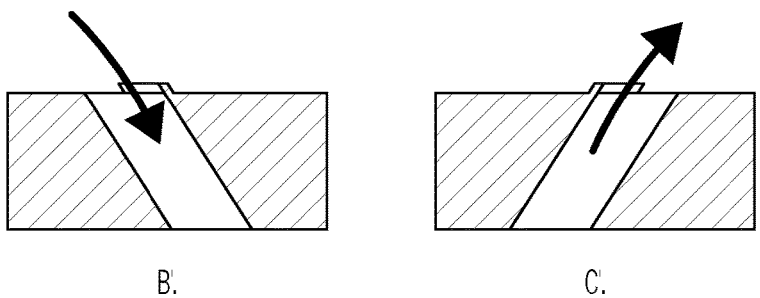
FIG. 7B is a cross sectional view comparing airflow thru orthogonal vent holes to airflow thru oblique vent holes having raised cowlings (shoulders)

FIG. 7B, Sketches B' and C' represent air vents having raised cowlings (shoulders) to redirect even more air (represented by the heaviest arrows) respectively downward into the vent and upward out of the vent). Additionally, vent hole configurations, including but not limited to a plurality of arrays of both B and C style vent holes are to encourage an increased path of airflow, for example, both into (supply) and out of (return), the area between the massage pad and the massage pad cover.

Figure 8A:
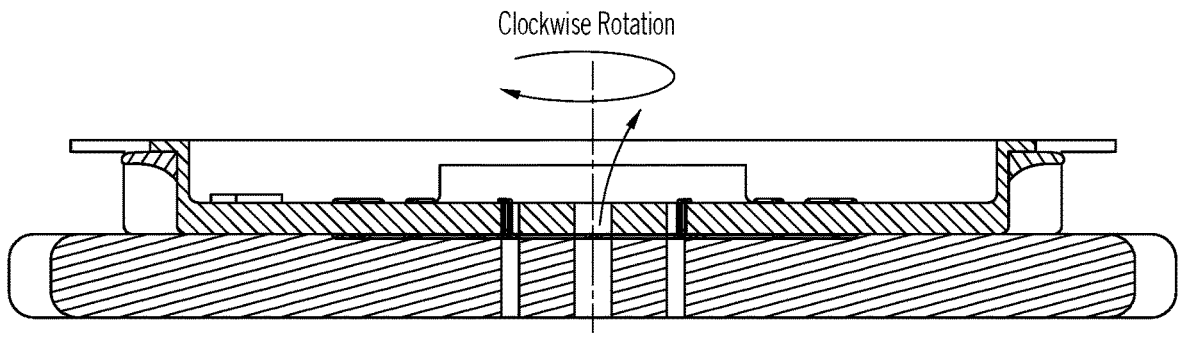
FIG. 8A is a cross sectional view of a contact surface arrangement having orthogonal vent holes.

FIG. 8A is a cross sectional view of a contact surface arrangement 40b having orthogonal vent holes. Such vent holes direct air flow in a direction orthogonal to a surface of a contact surface arrangement.

Figure 8B:
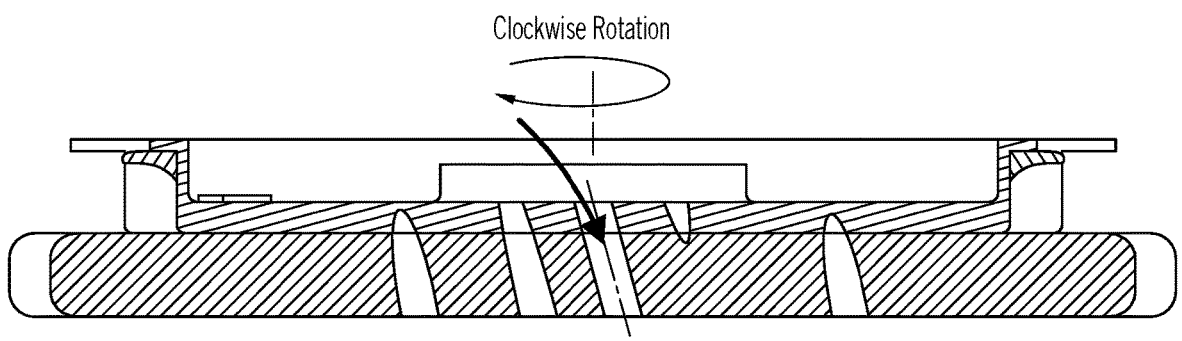
FIG. 8B is a cross sectional view of a contact surface arrangement having oblique vent holes slanted toward the direction of contact surface arrangement rotation.

FIG. 8B is a cross sectional view of a contact surface arrangement 40b, having oblique vent holes slanted toward the direction of contact surface arrangement 40b rotation. The vent holes, for example, direct air flow in an oblique angle (greater than zero degrees and less than ninety degrees) direction relative to an orthogonal to the surface of a contact surface arrangement.

Figure 8C:
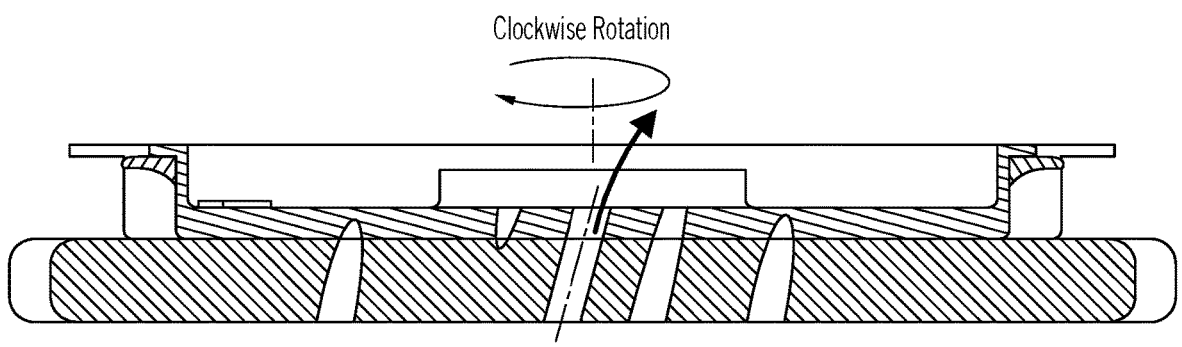
FIG. 8C is a cross sectional view of a contact surface arrangement having oblique vent holes slanted away from the direction of contact surface arrangement rotation.

FIG. 8C is a cross sectional view of a contact surface arrangement 40b, having oblique vent holes slanted away from the direction of contact surface arrangement 40b rotation. The vent holes, for example, direct air flow in an oblique angle (greater than zero degrees and less than ninety degrees) direction relative to an orthogonal to the surface of a contact surface arrangement. As described above, a plurality of arrays of both B' and C' style vent holes are used to encourage an increased path of airflow, for example, both into (supply) and out of (return), the area between the massage pad 8 and the massage pad cover 9, which are designed to maximize massage head cooling by means of maximizing ventilation.

FIGS. 8A, 8B, and 8C show airflow thru the massage pad assembly 40b with orthogonal vents (FIG. 8A), vents angled in the direction of rotation of the massage pad assembly 40b (FIG. 8B), and vents angled opposite to the direction of rotation of the massage pad assembly 40b (FIG. 8C). Heavier arrow line widths indicate increased airflow thru vents.

The above description of vent holes, their styles, angles, configuration(s) and their utilization as shown in FIGS. 7A and 7B and as utilized in the massage pad assembly 40b as shown in FIGS. 8A, 8B, and 8C are examples, and are not intended to limit other possible vent hole design styles, configurations, or utilization.

Figure 9A:
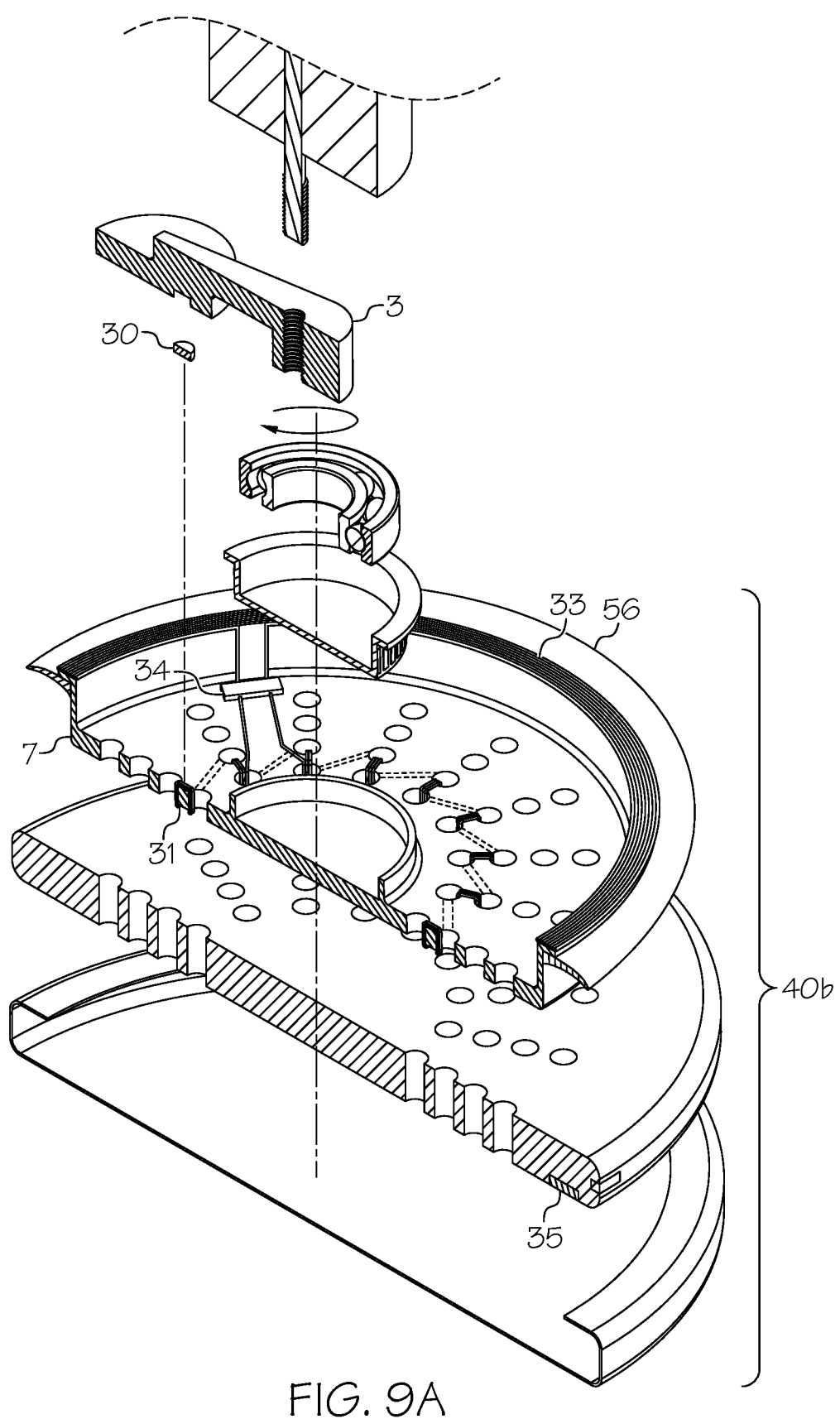
FIGS. 9A, 9B, 9C, and 9D are section drawings showing one embodiment of inductive coupling of data or control signals and power between the drive assembly and the massage pad assembly of the example motorized therapeutic massage device of FIG. 1.
Figure 9B:
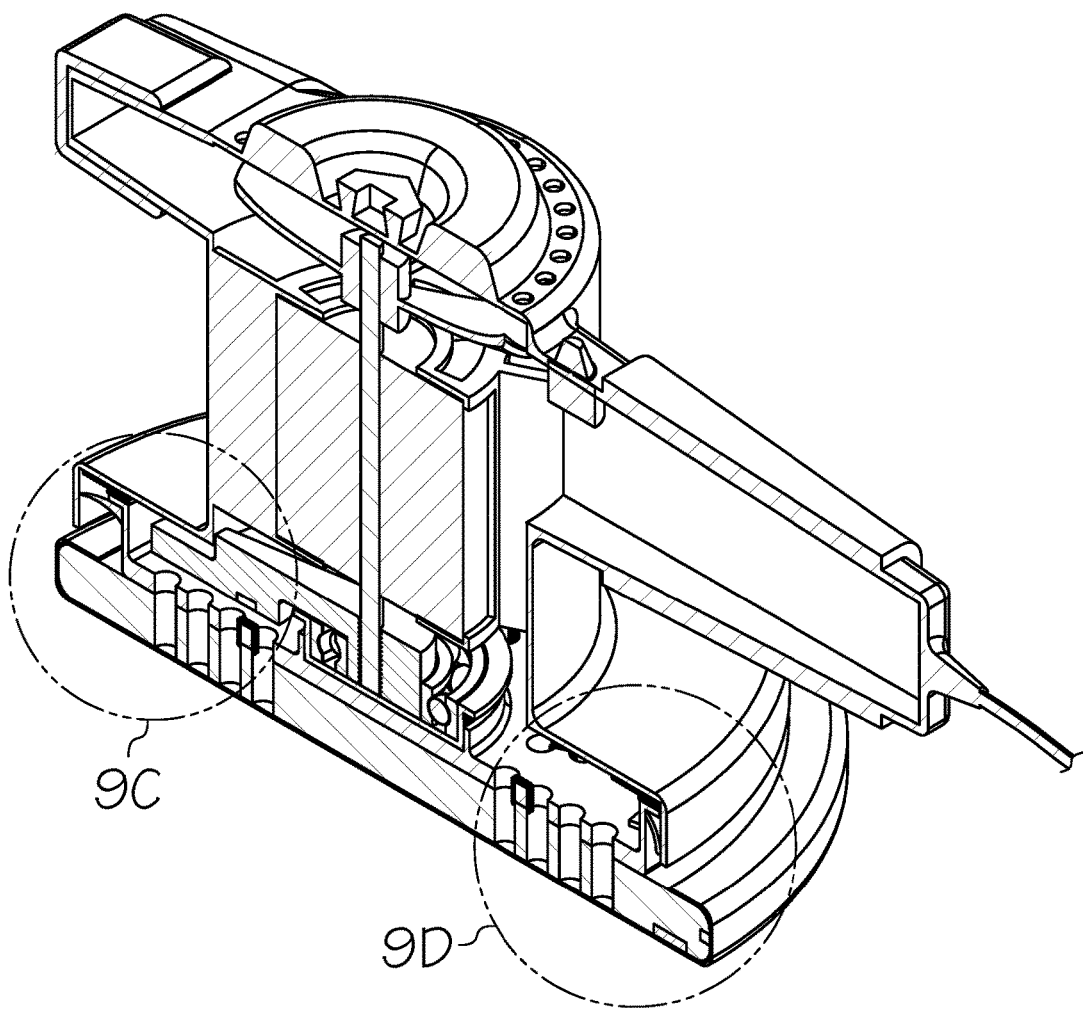
Figure 9C:
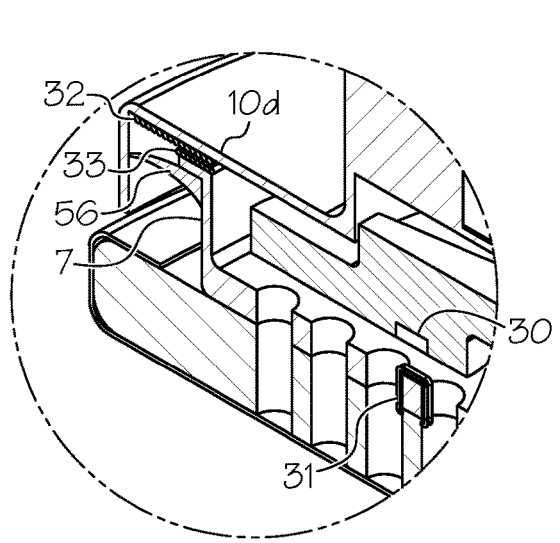
Figure 9D:
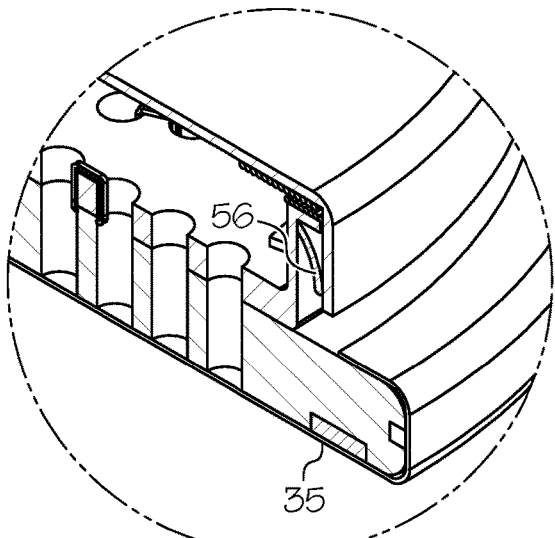
Figure 9E:
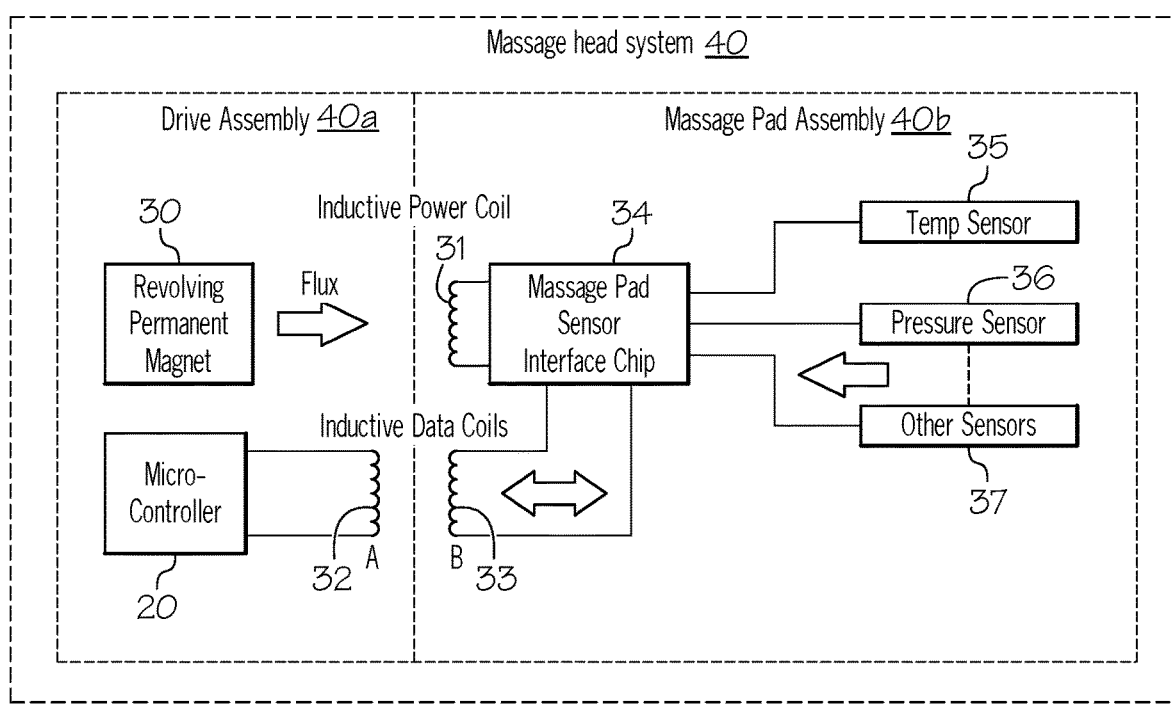
FIG. 9E is a block diagram showing one embodiment of inductive coupling of power and data between the drive assembly and the massage pad assembly.

FIG. 9E is a block diagram showing one embodiment of inductive coupling of power and data between the drive assembly and the massage pad assembly. When power is switched ON to the motor of the massage device within the drive assembly 40a, the magnetic field from the permanent magnet 30 disposed on the offset hub 3, when spinning, induces a current to flow in the inductive power coil 31, producing power to the massage pad sensor interface chip 34, disposed upon the massage pad assembly 40b. The massage pad sensor interface chip 34, now receiving signals from at least one of a plurality of sensors disposed upon the massage pad assembly 40b is transmitted by means of the inductive data coil A 32, and inductive data coil B 33 to the micro controller 20 disposed within the drive assembly 40a of the massage head.

FIG. 9A is an exploded section drawing showing one embodiment of a fixed magnet inducing power in the inductive power coil. When power is switched on to the motor 1 of the massage device within the drive assembly 40a (not shown in this figure), the magnetic field from the permanent magnet 30 disposed on the offset hub 3, when spinning, induces a current to flow in the inductive power coil 31, producing power to the massage pad sensor interface chip 34, disposed upon the massage pad mounting plate 7. The massage pad sensor interface chip 34, now receiving signals from at least one 35 of a plurality of sensors disposed upon the massage pad assembly 40b is transmitted by means of the inductive data coil A 32, and inductive data coil B 33 to the micro controller 20 disposed within the drive assembly 40a (not shown in this figure) of the massage device.

FIG. 9B is a cross sectional view of an inductive power circuit and an inductive data circuit transmitting power to the massage pad assembly and temperature data from the massage pad assembly to the massage device. For detailed descriptions, see partial enlarged view drawing FIGS. 9C and 9D.

Partial enlarged view drawing FIG. 9C shows permanent magnet 30 aligned above inductive power coil 31. As more clearly seen in FIG. 9A, inductive power coil 31 induces power into massage pad sensor interface chip 34, (not visible in this view). Temperature data from massage pad temp sensor 35 is coupled from the massage pad temp sensor 35 to the microprocessor of microcontroller 20 via the massage pad sensor interface chip 34, the inductive data coil B 33 disposed on the massage pad mounting plate 7, which inductively couples temperature data to inductive data coil A 32 disposed on the bottom surface of the enclosure shroud 10d, ultimately coupling to the microprocessor of microcontroller 20 (not shown in FIG. 9C).

Partial enlarged view drawing FIGS. 9C and 9D illustrate an example of an entanglement reduction seal 56, which reduces the risk of a user having hair or clothing enter into the interior of the enclosure and becoming entangled around the offset hub 3 or the motor drive shaft 2. Eccentric motion of the offset hub 3 results in the entanglement reduction seal 56 to fill the longer gap as seen in FIG. 9C and to compress within the shorter gap as seen in FIG. 9D.

Figure 10:
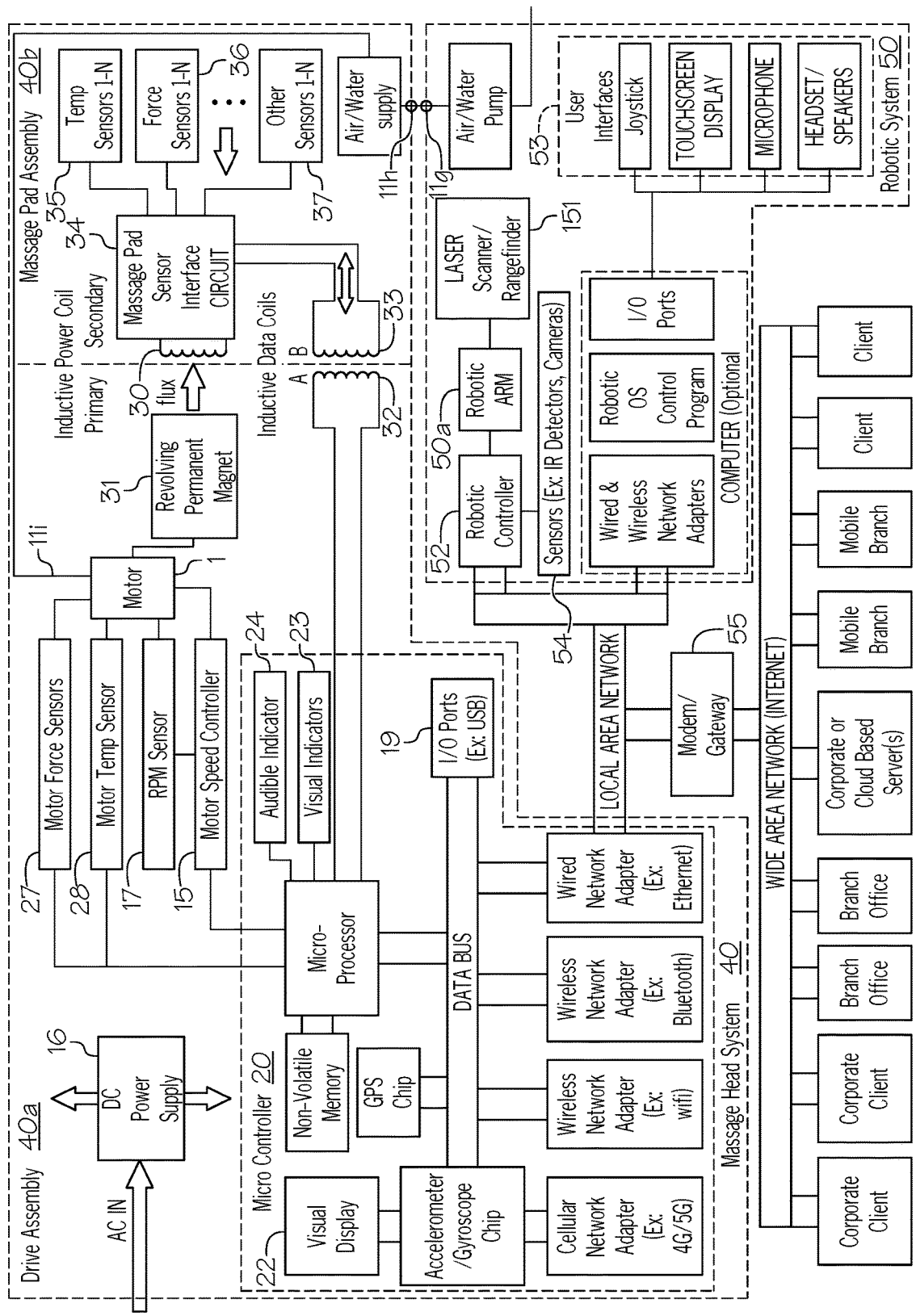
FIG. 10 is a block diagram showing a networked robotic massage system.

FIG. 10 is a block diagram showing the networked robotic massage system, comprised of the massage head 40 and the robotic system 50. The user, logs in to his account via the touchscreen display user interface 53, to initiate his massage therapy session, then chooses from a plurality of predetermined default massage programs, or a predetermined custom massage program. The massage head 40 which is comprised of the drive assembly 40a, which mechanically, electrically and electronically, (or via air or water detachably supplied through air/fluid couplers 11g and 11h, and via air/fluid line(s) 11i) enables the massage pad assembly 40b, to activate. The robotic controller 52 instructs the robot arm 50a to execute the chosen massage program to move the massage pad assembly 40b safely over the user, as per the predetermined paths, pressures, speeds and treatment times, and temperatures detected by infrared detectors, cameras or other sensors 54 specified by the user chosen massage program. Data logged with respect to the location, position and pressure of the massage pad 50 upon the user, and topographical data of the user provided by laser scanner 151 and user massage preferences will be stored to develop a user profile, so as to improve the massage experience for each user. For security, user profiles will be synced to corporate offices, branch offices or corporate and cloud based servers. AI (Artificial Intelligence) and machine learning algorithms will analyze logged data including, but not limited to: clinical research regarding chronic pain, pain reduction and increased degrees of mobility, increased productivity and corporate moral.

Figure 11:
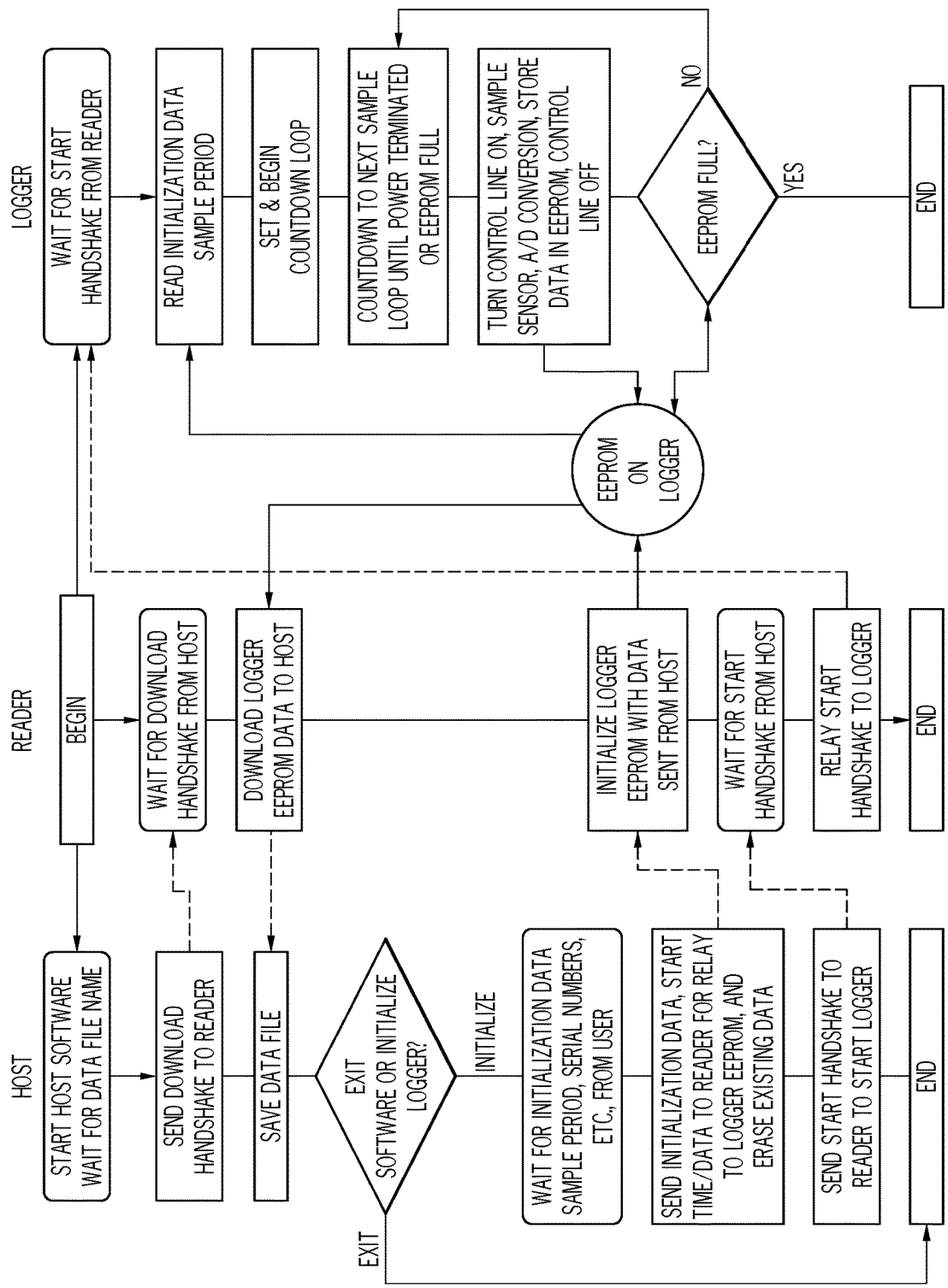
FIG. 11 is a diagram showing one embodiment of a software operational flow and handshaking of data and/or control signals; in accordance with the example motorized therapeutic massage device of FIG. 1.

FIG. 11 is a diagram showing one embodiment of a data logger with handshaking software flow chart. Data logging is well known to one of ordinary skill in the art. This is but one example of a software data logger that can be employed herein.

According to various embodiments, a mobile service including but not limited to a massage therapist come on site to provide massage services at various venues, including workplaces or conventions, performing massage services on attendees positioned on both massage chairs and massage tables.

Certain embodiments may include attachment of the device to a multiple-axis robotically controlled system 50, having an emergency stop switch (not shown), which is well known in the manufacturing industry, and is routinely used for computer numerically controlled (CNC) milling processes, using 3-dimensional space, as defined by the Cartesian coordinate system. This aspect includes, but is not limited to a computer controlled robotic arm, a combination of gantry arms, or the like, attached to the massage device discussed above. An example embodiment of such a system stores patient profiles that for each patient can include, but is not limited to, account information, medical records, body topography, preferences for programmed default and personalized massage paths, RPM speeds, rate of travel (feeds), contact surface pressure, angles of tilt and rotation, and exclusion areas.

Such embodiments may include either manually mapping the topography of the patient, using methods including but not be limited to capturing spatial data points (known as digitizing) by moving the massage pad over the body, by means of a joystick controller to mapping the topography of the patient using a laser scanner. Additionally, audio and video data can be captured when a patient is receiving treatment. Another aspect may include, but not be limited to, a plurality of massage centers located in airports or other locations connected via a computer network that could provide the patient at any of the locations with individualized massage therapy program. This would allow weary travelers to receive their desperately needed massage just the way they like it, no matter where in the world they are.

Like the mobile service described above, one or more robotically controlled systems 50 could be disposed within or upon a mobile vehicle 57, including but not limited to a van, a mobile home, a recreational vehicle, or travel trailer or a motorized platform. One such embodiment includes, but is not limited to: sporting events, concerts, special events, and corporate events. Patient profiles would be accessed via wireless cellular networks.

One embodiment of such a system can include, but is not limited to: a web based scheduling system that allows the user to find locations, schedule appointments for both manual and robotic massage sessions, and pay via the user's smart phone, or robotic system.

One should note that the above described various example embodiments of the invention, are for illustration purposes only, and are not for the purpose of limiting its scope. The various examples teach various changes in form, details, improvements and other embodiments that may be equally effective. Such improvements are intended to be part of this disclosure without departing from the scope of the invention as defined by the appended claims.

Non-Limiting Examples

Flowchart and block diagrams that may be shown in the Figures and/or described herein illustrate the architecture, functionality, and operation of possible implementations of systems, devices, and methods, according to various embodiments of the present invention. In this regard, each block in a flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although the present specification may describe components and functions implemented in the embodiments with reference to particular standards and protocols, the disclosure is not limited to such standards and protocols. Each of the standards represents an example of the state of the art. Such standards are from time-to-time superseded by faster or more efficient equivalents having essentially the same functions.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The term "communicatively coupled" or "communicatively coupling" includes, but is not limited to, communicating electronic control signals by which one element may direct or control another. The term "configured to" describes hardware, software or a combination of hardware and software that is adapted to, set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

What is claimed is:

1. A motorized therapeutic massage device comprising:
a motor having a motor drive shaft, disposed within an enclosure,
a contact surface of a contact surface arrangement is coupled to said motor drive shaft, by means of a transfer member disposed within the enclosure, a hub axis of the transfer member is offset from the center axis of the motor drive shaft and the center axis of the contact surface,
and wherein the motor and driveshaft are coupled to drive the contact surface to impart both random orbital oscillating motion and percussive motion to the contact surface,
and wherein the contact surface is adapted to create a penetrating shockwave subcutaneously through human or animal muscle tissue, and is adapted to reduce the frictional engagement of skin or garments covering skin,
and wherein at least one sensor is coupled to the contact surface arrangement and the at least one sensor is communicatively coupled to a microprocessor of the motorized therapeutic massage device; and further comprising:
a quick disconnect mount for mechanically mounting the motorized therapeutic massage device as a massage head end effector on a robot arm of a robotically controlled system, the quick disconnect mount including
electrical connectors for communicating any of electrical power signal, data signals, or control signals, or any combination thereof, and
air or fluid channel couplers for transferring air or fluid or both, between the motorized therapeutic massage device as a massage head end effector and the robot arm; and
the robotically controlled system including electrical connections for mating with the electrical connectors of the quick disconnect mount and air or fluid lines for mating with the air or fluid channel couplers of the quick disconnect mount, and thereby coupling signals and air or fluid with the motorized therapeutic massage device, the robotically controlled system including a 5-axis joystick coupled to a programmable computer including a controller and a multi-axis control head, to selectively provide power to the motor of the motorized therapeutic massage device and to move the motorized therapeutic massage device through space in three spatial dimensions (X, Y, and Z), thereby to provide a full body massage, having the ability to tilt, rotate, and move through space, the motorized therapeutic massage device.

2. The motorized therapeutic massage device of claim 1, wherein the contact surface arrangement includes a massage pad and a massage pad cover,
and wherein a plurality of air vents disposed on the contact surface arrangement, while it is in such random orbital oscillating motion and percussive motion, direct airflow to the contact surface thereby cooling the contact surface,
and wherein the plurality of air vents comprises a plurality of oblique angled vent holes,
and wherein the massage pad has the plurality of oblique angled vent holes to direct airflow into or out from the oblique angled vent holes while disposed within the contact surface arrangement to reduce the temperature of the contact surface of the contact surface arrangement,
and wherein the oblique angled vent holes disposed within the massage pad of the contact surface arrangement direct airflow to or from, and thereby to cool, cooling of the massage pad cover of the contact surface arrangement.

3. The motorized therapeutic massage device of claim 1, wherein the at least one sensor comprises a plurality of sensors coupled to an indicator or indicators.

4. The motorized therapeutic massage device of claim 1 wherein the contact surface comprises a multilayered component comprising a rigid disk, a layer of cellular foam or rubber, and a cover, the cover including at least one material selected from the following set of materials consisting of:

leather, woven cloth, and vinyl, each of the aforementioned materials being non-perforated, or each of the aforementioned materials being perforated.

5. The motorized therapeutic massage device of claim 1 wherein the contact surface comprises a cover selected from a plurality of removable contact surface covers that include one or more contact surfaces having a low coefficient of friction where the one or more contact surfaces are adapted to contact a skin surface of a patient, and the contact surface covers include perforations to improve airflow through the perforations thereby a) reducing contact surface cover temperature, b) improving sensitivity of contact surface pressure mapping of the skin surface of the patient, or both a) and b).

6. A motorized therapeutic massage device comprising:
a motor having a motor drive shaft, disposed within an enclosure,
a contact surface of a contact surface arrangement is coupled to said motor drive shaft, by means of a transfer member disposed within the enclosure, a hub axis of the transfer member is offset from the center axis of the motor drive shaft and the center axis of the contact surface,
and wherein the motor and driveshaft are coupled to drive the contact surface to impart both random orbital oscillating motion and percussive motion to the contact surface,
and wherein the contact surface is adapted to create a penetrating shockwave subcutaneously through human or animal muscle tissue, and is adapted to reduce the frictional engagement of skin or garments covering skin,
and wherein a plurality of air vents disposed upon the contact surface arrangement, while the contact surface is in such random orbital oscillating motion and percussive motion, direct airflow to the contact surface thereby cooling the contact surface; and further comprising:
a quick disconnect mount for mechanically mounting the motorized therapeutic massage device as a massage head end effector on a robot arm of a robotically controlled system, the quick disconnect mount including
electrical connectors for communicating any of electrical power signal, data signals, or control signals, or any combination thereof, and
air or fluid channel couplers for transferring air or fluid or both, between the motorized therapeutic massage device as a massage head end effector and the robot arm; and
the robotically controlled system including electrical connections for mating with the electrical connectors of the quick disconnect mount and air or fluid lines for mating with the air or fluid channel couplers of the quick disconnect mount, and thereby coupling signals and air or fluid with the motorized therapeutic massage device, the robotically controlled system including a 5-axis joystick coupled to a programmable computer including a controller and a multi-axis control head, to selectively provide power to the motor of the motorized therapeutic massage device and to move the motorized therapeutic massage device through space in three spatial dimensions (X, Y, and Z), thereby to provide a full body massage, having the ability to tilt, rotate, and move through space, the motorized therapeutic massage device.

7. The motorized therapeutic massage device of claim 6, including at least one sensor movably coupled to the contact surface, the programmable computer of the robotically controlled system being configured to, in response to executing computer instructions,
contact an area of skin covered human, or animal, muscle tissue having muscle tension or soreness, with the contact surface of the contact surface arrangement;
the motor, in response to being powered, couple orbital oscillating motion to the contact surface arrangement;
apply, by the contact surface in response to the motor being powered, orbital oscillating motion energy to the skin covered human, or animal, muscle tissue, the orbital oscillating motion energy being applied in both parallel and perpendicular motion components relative to a surface of the skin covered human, or animal, muscle tissue thereby inducing shearing and stretching forces in the muscle tissue; and
map, by the at least one sensor sensing applied pressure of such forces at the contact surface while contacting the skin, the applied pressure of such forces on a topography of the skin.

8. The motorized therapeutic massage device of claim 7, wherein the at least one sensor including a temperature sensor coupled to the contact surface for sensing temperature corresponding to the contact surface of the contact surface arrangement while the orbital oscillating motion energy is adapted to being applied to the surface of the skin covered human, or animal, muscle tissue.

9. The motorized therapeutic massage device of claim 7, including a microphone communicatively coupled to the robotically controlled system to capture audio data of a patient while receiving treatment with the motorized therapeutic massage device.

10. The motorized therapeutic massage device of claim 7, including a camera communicatively coupled to the robotically controlled system to capture video data of a patient while receiving treatment with the motorized therapeutic massage device.

11. The motorized therapeutic massage device of claim 7, including a network interface communicatively coupled with the programmable computer to communicate data captured from the at least one sensor, contemporaneous with a patient receiving treatment with the motorized therapeutic massage device, via a computer network to a cloud based server for storage of the captured data at a storage resource of the server.

12. The motorized therapeutic massage device of claim 7, wherein the motorized therapeutic massage device and the robotically controlled system are disposed within or upon a mobile operations vehicle or a mobile platform.

13. A motorized therapeutic massage device comprising:
a motor having a motor drive shaft, disposed within an enclosure,
a contact surface of a contact surface arrangement coupled to said motor drive shaft, by means of a transfer member disposed within the enclosure, a hub axis of the transfer member is offset from the center axis of the motor drive shaft and the center axis of the contact surface,
and wherein the motor and driveshaft are coupled to drive the contact surface to impart both random orbital oscillating motion and percussive motion to the contact surface,
and wherein the contact surface is adapted to create a penetrating shockwave subcutaneously through human or animal muscle tissue, and is adapted to reduce the frictional engagement of skin or garments covering skin, and wherein at least one sensor is coupled to the contact surface of the contact surface arrangement and the at least one sensor is communicatively coupled to a microprocessor of the motorized therapeutic massage device; and further comprising:

a quick disconnect mount for mechanically mounting the motorized therapeutic massage device as a massage head end effector on a robot arm of a robotically controlled system, the quick disconnect mount including electrical connectors for communicating any of electrical power signal, data signals, or control signals, or any combination thereof, and air or fluid channel couplers for transferring air or fluid or both, between the motorized therapeutic massage device as a massage head end effector and the robot arm; and the robotically controlled system including electrical connections for mating with the electrical connectors of the quick disconnect mount and air or fluid lines for mating with the air or fluid channel couplers of the quick disconnect mount, and thereby coupling signals and air or fluid with the motorized therapeutic massage device, the robotically controlled system including a 5-axis joystick coupled to a programmable computer including a controller and a multi-axis control head, to selectively provide power to the motor of the motorized therapeutic massage device and to move the motorized therapeutic massage device through space in three spatial dimensions (X, Y, and Z), thereby to provide a full body massage, having the ability to tilt, rotate, and move through space, the motorized therapeutic massage device.

14. The motorized therapeutic massage device of claim 13, wherein the at least one sensor comprises a plurality of sensors to measure at least one state of properties associated with the contact surface, including temperature or pressure.

* * * * *